US012759981B2

(12) United States Patent
Bäurle et al.

(10) Patent No.: US 12,759,981 B2
(45) Date of Patent: Oct. 13, 2026

(54) CHOLINATE OF 2-(1-CYCLOBUTYL-1H-PYRAZOL-4-YL)-5-[([{1-[2-FLUORO-4-(TRIFLUOROMETHYL)-PHENYL] CYCLOPROPYL}CARBONYL)AMINO] BENZOIC ACID

(71) Applicant: Bayer Aktiengesellschaft, Leverkusen (DE)

(72) Inventors: Stefan Bäurle, Berlin (DE); Hans-Georg Lerchen, Leverkusen (DE); Britta Olenik, Bottrop (DE); Guillaume Levilain, Wuppertal (DE); Birgit Keil, Düsseldorf (DE); Sylvia Dworacek, Solingen (DE); Antje Rottmann, Berlin (DE); Andrea Rotgeri, Berlin (DE); Robert Craig Melling, Oxfordshire (GB)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 93 days.

(21) Appl. No.: 18/572,042

(22) PCT Filed: Jul. 4, 2022

(86) PCT No.: PCT/EP2022/068421
§ 371 (c)(1),
(2) Date: Dec. 19, 2023

(87) PCT Pub. No.: WO2023/280765
PCT Pub. Date: Jan. 12, 2023

(65) Prior Publication Data
US 2025/0282734 A1 Sep. 11, 2025

(30) Foreign Application Priority Data
Jul. 5, 2021 (EP) .................................... 21183771

(51) Int. Cl.
*C07D 231/12* (2006.01)
*A61K 31/415* (2006.01)

(52) U.S. Cl.
CPC .......... *C07D 231/12* (2013.01); *A61K 31/415* (2013.01)

(58) Field of Classification Search
CPC ............................ C07D 231/12; A61K 31/415
USPC .......................................................... 514/406
See application file for complete search history.

(56) References Cited

U.S. PATENT DOCUMENTS 11,905,270 B2 2/2024 Baeurle et al.

FOREIGN PATENT DOCUMENTS

| | | | |
|---|---|---|---|
| DE | 19624155 | A1 | 1/1998 |
| WO | 03065789 | A2 | 8/2003 |
| WO | 2007087006 | A2 | 8/2007 |
| WO | 2009036996 | A2 | 3/2009 |
| WO | 2012059776 | A1 | 5/2012 |
| WO | 2012103583 | A1 | 8/2012 |
| WO | 2012112363 | A1 | 8/2012 |
| WO | 2012112567 | A1 | 8/2012 |
| WO | 2017172596 | A1 | 10/2017 |
| WO | 2018114786 | A1 | 6/2018 |
| WO | 2018115466 | A1 | 6/2018 |

OTHER PUBLICATIONS

Degenerative Nerve Diseases [online], [retrieved on Nov. 24, 2025] Retrieved from the Internet, URL: https://medlineplus.gov/degenerativenervediseases.htm (Year: 2025).*
Walter A. S. Moraes, Current Pharmacological and Non-Pharmacological Therapies for Neurodegenerative Diseases, 2015, Young Perspectives for Old Diseases, 23-48 (Year: 2015).*
Phagoo, Stephen B., et al., "Autoregulation of Bradykinin Receptors: Agonists in the Presence of Interleukin-1ß Shift the Repertoire of Receptor Subtypes from B2 to B1 in Human Lung Fibroblasts," Molecular Pharmacology, (1999), vol. 56: 325-333.
Prado, Gregory N., et al., "Mechanisms Regulating the Expression, Self-Maintenance, and Signaling-Function of the Bradykinin B2 and B1 Receptors," Journal of Cellular Physiology, (2002), vol. 193: 275-286.
Pure Appl Chem, (19760000), vol. 45, pp. 11-30.
Schneider, F. et al. (2006) "Enhanced Plasma Concentration by Selective Deuteration of Rofecoxib in Rats," Arzneim. Forsch./Drug Res., 56(4):295-300.

(Continued)

*Primary Examiner* — Kristin A Vajda

(57) ABSTRACT

The present invention relates to the choline salt (cholinate) of 2-(1-cyclobutyl-1H-pyrazol-4-yl)-5-[({1-[2-fluoro-4-(trifluoromethyl)-phenyl]cyclopropyl}carbonyl)amino]benzoic acid. In particular, the invention relates to the compound according to formula (II):

(II)

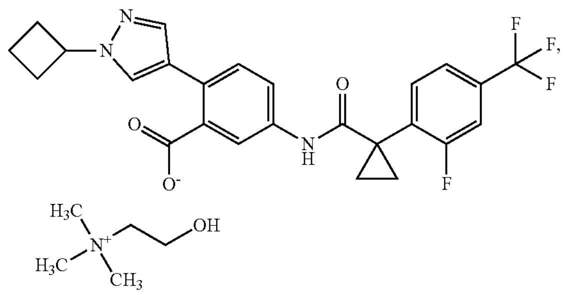

Figure 1:
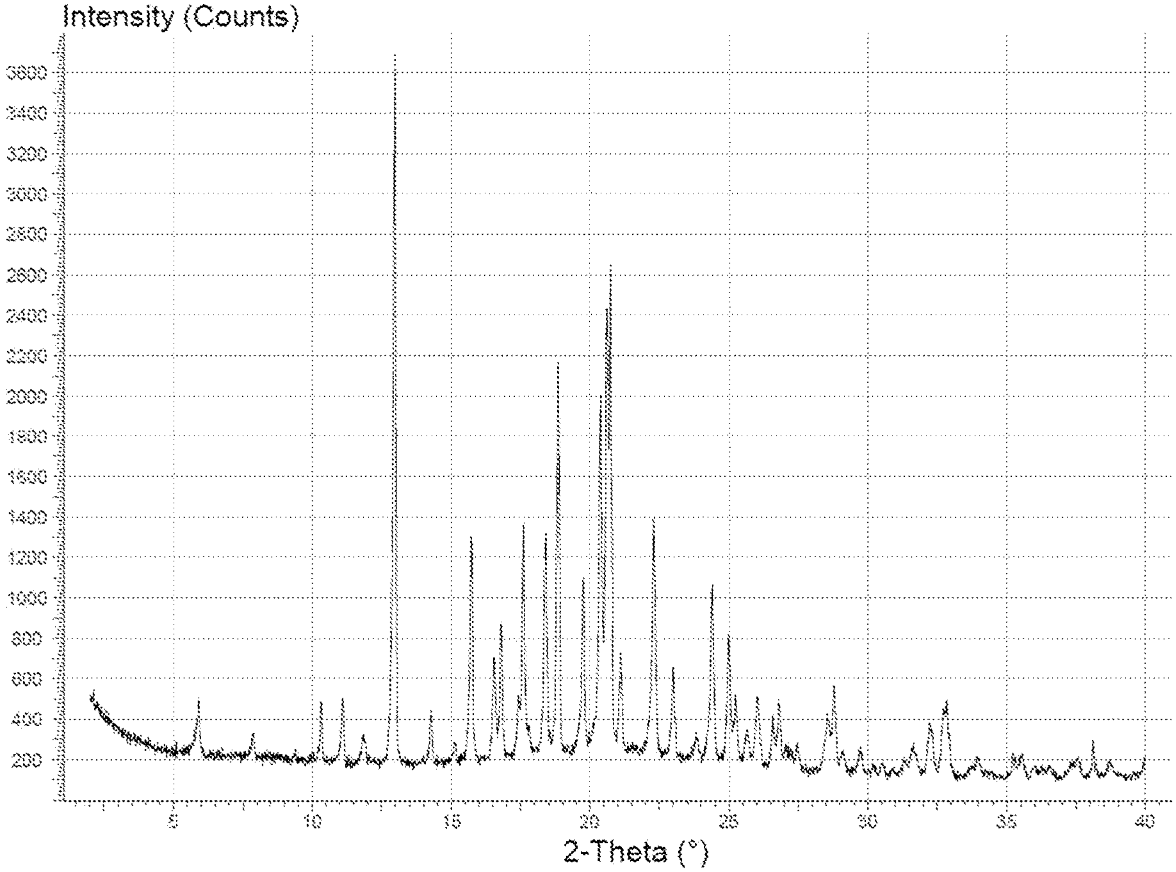

or a tautomer, solvate or hydrate thereof, as well as to medical uses of the cholinate according to the invention.

18 Claims, 21 Drawing Sheets

(56) References Cited

OTHER PUBLICATIONS

Schremmer-Danninger, et al., "Visualisation of tissue kallikrein, kininogen and kinin receptors in human skin following trauma and in dermal diseases," Biol. Chem., (2004), vol. 385: 1069-1076.
Schuelert, N. et al., "The bradykinin B1 receptor antagonist BI113823 reverses inflammatory hyperalgesia by desensitization of peripheral and spinal neurons," European Journal of Pain, (2015), vol. 19: 132-142.
Sharma, A. et al. (2013) "Nevirapine Bioactivation and Covalent Binding in the Skin," Chem Res Toxicol; 26:410-421.
Silva, et al., "The role of kinin B1 receptor and the effect of angiotensin I-converting enzyme inhibition on acute gout attacks in rodents," Ann Rheum Dis, (2016), vol. 75: 260-268.
Simoens, et al., "The burden of endometriosis: costs and quality of life of women with endometriosis and treated in referral centres," Human Reproduction, (2012), vol. 27, No. 5: 1292-1299.
Stratton, et al., "Chronic pelvic pain and endometriosis: translational evidence of the relationship and implications," Human Reproduction Update, (2011), vol. 17, No. 3: 327-346.
Tayar, N. et al. (1984) "The lipophilicity of deuterium atoms. A comparison of shake-flask and HPLC methods," Int J Pharm; 19{3), 271-281.
Walsh, David A., et al., "Tachykinis and the Cardiovascular System," Current Drug Targets, (2006), vol. 7: 1031-1042.
Wang, et al., "Deletion of bradykinin B1 receptor reduces renal fibrosis," International Immunopharmacology, (2009), vol. 9: 653-657.
Wenthur, C. et al. (2013) "Discovery of {R)-{2-Fiuoro-4-{{-4-methoxyphenyl)ethynyl)phenyl) {3-Hydroxypiperidin-1-yl) methanone {ML337), An mGiu3 Selective and CNS Penetrant Negative Allosteric Modulator (NAM)," J Med Chern; 56:5208-5212.
Westermann, Dirk, et al., "Gene Deletion of the Kinin Receptor B1 Attenuates Cardiac Inflammation and Fibrosis During the Development of Experimental Diabetic Cardiomyopathy," Diabetes, (2009), vol. 58: 1373-1381.
Wu-Wong, et al., "Endothelin Receptor Antagonists: Effect of Serum Albumin on Potency and Comparison of Pharmacological Characteristics," Journal of Pharmacology and Experimental Therapeutics, (1997), vol. 281, No. 2: 791-798.
Yoshino, et al., "The expression and the role of bradykinin {BK) receptor in endometriosis," Abstracts/Journal of Reproductive Immunology, (2015), vol. 112: 121-140.
Yoshiyama, et al., "Role of spinal α1-adrenoceptor subtypes in the bladder reflex in anesthetized rats," Am. J. Physiol. Regulatory Integrative Comp. Physiol., (2001), vol. 280: R1414-R1419.
Bascands, et al., "Molecular determinants of LPS-induced acute renal inflammation: Implication of the kinin B1 receptor," Biochemical and Biophysical Research Communications, (2009), vol. 386: 407-412.
Belichard, et al., "Pharmacological and molecular evidence for kinin B1 receptor expression in urinary bladder of cyclophosphamide-treated rats," British Journal of Pharmacology, (1999), vol. 128: 213-219.
Berge S.M., et al., "Pharmaceutical Salts," Journal of Pharmaceutical Sciences, Jan. 1977, vol. 66 (1), pp. 1-19.
Bertram, et al., "Expression of kinin receptors on eosinophils: comparison of asthmatic patients and healthy subjects," Journal of Leukocyte Biology, (2009), vol. 85: 544-552.
Bioorganic and Medicinal Chemistry Letters, (20110000), vol. 21, pp. 5502-5505.
Bozo, et al., "Bradykinin B1 receptor antagonists: a patent update 2009-2012," Expert Opinion on Therapeutic Patents, (2012), vol. 22, No. 12: 1443-1452.
Breivik, et al., "Survey of chronic pain in Europe: Prevalence, impact on daily life, and treatment," European Journal of Pain, (2006), vol. 10: 287-333.
Campos, et al., "Non-peptide antagonists for kinin B1 receptors: new insights into their therapeutic potential for the management of inflammation and pain," TRENDS in Pharmacological Sciences, (2006), vol. 27, No. 12: 646-651.
Cassim, et al., "Kallikreins, kininogens and kinin receptors on circulating and synovial fluid neutrophils: role in kinin generation in rheumatoid arthritis," Rheumatology, (2009), vol. 48: 490-496.
Chen, Jian Jeffrey, et al., "Targeting the bradykinin B1 receptor to reduce pain," Expert Opinion on Therapeutic Targets, (2007), vol. 11, No. 1: 21-35.
Da Costa, et al., "The role of kinin receptors in cancer and therapeutic opportunities," Cancer Letters, (2014), vol. 345: 27-38.
De Graaff, et al., "The significant effect of endometriosis on physical, mental and social wellbeing: results from an international cross-sectional survey," Human Reproduction, (2013), vol. 28, No. 10: 2677-2685.
Dias, et al., "Blockade of kinin B1 receptor reverses plasma fatty acids composition changes and body and tissue fat gain in a rat model of insulin resistance," Diabetes, Obesity and Metabolism, (2012), vol. 14: 244-253.
Dias, et al., "Suppression of Vascular Inflammation by Kinin B1 Receptor Antagonism in a Rat Model of Insulin Resistance," Journal of Cardiovascular Pharmacology, (2012), vol. 60, No. 1: 61-69.
Dias, JP, et al., "The kinin B1 receptor antagonist SSR240612 reverses tactile and cold allodynia in an experimental rat model of insulin resistance," British Journal of Pharmacology, (2007), vol. 152: 280-287.
Eisenbarth, et al., "Sensitization to bradykinin B1 and B2 receptor activation in UV-B irradiated human skin," Pain, (2004), vol. 110: 197-204.
Extended European Search Report from EP211837711 mailed Nov. 19, 2021.
Farkas, Sander, et al., "The therapeutic potential of bradykinin B1 inhibitors in chronic pain," Drugs of the Future, (2011), pp. 1-37.
Ferreira, et al., "Evidence for the participation of kinins in Freund's adjuvant-induced inflammatory and nociceptive responses in kinin B1 and B2 receptor knockout mice," Neuropharmacology, (2001), vol. 41: 1006-1012.
Ferreira, et al., "Reduced Nerve Injury-Induced Neuropathic Pain in Kinin B1 Receptor Knock-Out Mice," Journal of Neuroscience, (2005), vol. 25, No. 9: 2405-2412.
Fincham, Christopher I., et al., "Bradykinin receptor antagonists - a review of the patent literature 2005-2008," Expert Opinion on Therapeutic Patents, (2009), vol. 19, No. 7: 919-941.
Forner, et al., "Effects of kinin B1 and B2 receptor antagonists on overactive urinary bladder syndrome induced by spinal cord injury in rats," British Journal of Pharmacology, (2012), vol. 167: 1737-1752.
Fox, et al., "Antihyperalgesic activity of a novel nonpeptide bradykinin B1 receptor antagonist in transgenic mice expressing the human B1 receptor," British Journal of Pharmacology, (2005), vol. 144: 889-899.
Gao, et al., "Economic burden of endometriosis," Fertility and Sterility, (2006), vol. 86, No. 6: 1561-1572.
Gobeil Jr., et al., "Preclinical pharmacology, metabolic stability, pharmacokinetics and toxicology of the peptidic kinin B1 receptor antagonist R-954," Peptides, (2014), vol. 52: 82-89.
Gougat Jean, et al., "SSR240612 [(2R)-2-[((3R)-3-(1,3-Benzodioxol-5-yl)-3-{[(6-methoxy-2-naphthyl)sulfonyl] amino}propanoyl)amino]-3-(4-{[2R.6S)-2,6-dimethylpiperidinyl]methyl}phenyl)-N-isopropyl-N-methylpropanamide Hydrochloride], a New Nonpeptide Antagonist of the Bradykinin B1 Receptor: Biochemical and Pharmacological Characterization," Journal of Pharmacology and Experimental Therapeutics, (2004), vol. 309, No. 2: 661-669.
Hosogi, et al., "Bradykinin is a potent pruritogen in atopic dermatitis: A switch from pain to itch," Pain, (2006), vol. 126: 16-23.
Huart, et al., "Kinin B1 receptor antagonism is equally efficient as angiotensin receptor 1 antagonism in reducing renal fibrosis in experimental obstructive nephropathy, but is not additive," Frontiers in Pharmacology, (2015), vol. 6, No. 8: 1-8.
International Preliminary Report on Patentability from PCT Application No. PCT/EP2022/068421, Dec. 14, 2023.
International Search Report and Written Opinion from PCT Application No. PCT/EP2022/068421, Aug. 22, 2022.
International Search Report for PCT/EP2017/083290, mailed on Feb. 22, 2018.

(56) References Cited

OTHER PUBLICATIONS

Isotopic Compositions of the Elements 1997, Pure & Appl. Chem.; 1998; 70(1):217-235.
Jingwei, et al., "Effect of Bushenwenyanghuayu decoction on nerve growth factor and bradykinin/bradykinin B1 receptor in a endometriosis dysmenorrhea mouse model," Journal of Traditional Chinese Medicine, (2015), vol. 35, No. 2: 184-191.
Kaufman, et al., "Nociceptive tolerance is improved by bradykinin receptor B1 antagonism and joint morphology is protected by both endothelin type A and bradykinin receptor B1 antagonism in a surgical model of osteoarthritis," Arthritis Research Therapy, (2011), vol. 13, No. R76: 1-11.
Kilomentor, "The Complete Blog for the Preparation of Pharmaceutical Salts", kilmomentor.chemicalblogs.com, Feb. 11, 2008, retrieved from internet: URL: ttp://kilomentorchemicalblogs.com/55_kilomentor/archive/552_the_complete_blog_for_the_preparation_of_pharmaceutical_salts.html.
Lacoste, et al., "Cognitive and cerebrovascular improvements following kinin B1 receptor blockade in Alzheimer's disease mice," Journal of Neuroinflammation, (2013), vol. 10, No. 57: 1-18.
Laux-Biehlmann, et al., "Menstruation pulls the trigger for inflammation and pain in endometriosis," Trends in Pharmacological Sciences, (2015), vol. 36, No. 5: 270-276.
Leeb-Lundberg, L.M., et al., "International Union of Pharmacology. XLV. Classification of the Kinin Receptor Family: from Molecular Mechanisms to Pathophysiological Consequences," Pharmacological Reviews, (2005), vol. 57: 27-77.
Luiz, et al., "Contribution and Interaction of Kinin Receptors and Dynorphin a in a Model of Trigeminal Neuropathic Pain in Mice," Neuroscience, (2015), vol. 300: 189-200.
Maltais, F. et al. (2009) "In Vitro and In Vivo Isotope Effects with Hepatitis C Protease Inhibitors: Enhanced Plasma Exposure of Deuterated Telaprevir versus Telaprevir in Rats," J Med Chem; 52:7993-8001.
Marceau, Francois, "A possible common pharmacophore in the non-peptide antagonists of the bradykinin B1 receptor," TRENDS in Pharmacological Sciences, (2005), vol. 26, No. 3: 116-118.
Marceau, Francois, et al., "Bradykinin Receptor Ligands: Therapeutic Perspectives," Nature Reviews: Drug Discovery, (2004), vol. 3: 845-852.
Menke, John G., et al., "Expression Cloning of a Human B1 Bradykinin Receptor," Journal of Biological Chemistry, (1994), vol. 269, No. 34: 21583-21586.
Moyes, et al., "Bradykinin B1 receptor-mediated vasodilation is impaired in myometrial arteries from women with pre-eclampsia," Hypertension in Pregnancy, (2014), vol. 33, No. 2: 177-190.
Murugesan, et al., "Kinin B1 Receptor Inhibition With BI113823 Reduces Inflammatory Response, Mitigates Organ Injury, and Improves Survival Among Rats With Severe Sepsis," Journal of Infectious Diseases, (2016), vol. 213: 532-540.
Mutlib, A. et al. {2000) "The Species-Dependent Metabolism of Efavirenz Produces a Nephrotoxic Glutathione Conjugate in Rats," Toxicology and Applied Pharmacology; 169:102-113.
Parreiras-E-Silva, et al., "The kinin B1 receptor regulates muscle-specific E3 ligases expression and is involved in skeletal muscle mass control," Clinical Science, (2014), vol. 127: 185-194.
Passos, et al., "The Bradykinin B1 Receptor Regulates Aß Deposition and Neuroinflammation in Tg-SwDl Mice," The American Journal of Pathology, (2013), vol. 182, No. 5: 1740-1749.
Perrin, C. et al. (2005) "Stereochemistry of ß-Deuterium Isotope Effects on Amine Basicity," J. Am. Chem. Soc; 127: 9641-9647.
Perrin, C. et al.{2007) "Secondary Deuterium Isotope Effects on the Acidity of Carboxylic Acids and Phenols," JAm Chem Soc; 129:4490-4497.

* cited by examiner

CHOLINATE OF 2-(1-CYCLOBUTYL-1H-PYRAZOL-4-YL)-5-[([{1-[2-FLUORO-4-(TRIFLUOROMETHYL)-PHENYL]CYCLOPROPYL}CARBONYL)AMINO]BENZOIC ACID

The present invention relates to the choline salt (cholinate) of 2-(1-cyclobutyl-1H-pyrazol-4-yl)-5-[({1-[2-fluoro-4-(trifluoromethyl)-phenyl]cyclopropyl}carbonyl)amino]benzoic acid. 2-(1-cyclobutyl-1H-pyrazol-4-yl)-5-[({1-[2-fluoro-4-(trifluoromethyl)-phenyl]cyclopropyl}carbonyl)amino]benzoic acid is the compound of formula (I):

(I)

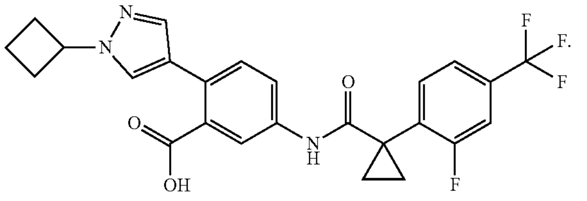

In particular, the invention relates to the choline salt of the compound of formula (I); or a solvate or hydrate thereof.

The invention relates to 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate (which is hereinafter referred to as "the cholinate of the present invention", or "the choline salt of the present invention"). The choline salt of the invention is the compound according to formula (II):

(II)

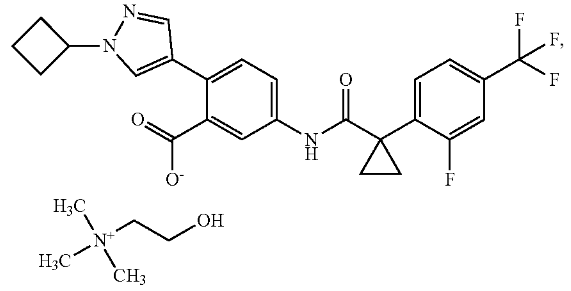

or a tautomer, solvate or hydrate thereof.

Further, the invention relates to

- a crystalline cholinate of 2-(1-cyclobutyl-1H-pyrazol-4-yl)-5-[({1-[2-fluoro-4-(trifluoromethyl)-phenyl]cyclopropyl}carbonyl)amino]benzoic acid (cholinate according to the present invention), preferably the crystalline cholinate of Form A;
- to methods of preparing said cholinate according to the present invention;
- to said cholinate according to the present invention for the treatment and/or prophylaxis of a disease;
- to the use of said cholinate according to the present invention for the preparation of a medicament for the treatment and/or prophylaxis of a disease;
- to a pharmaceutical composition comprising said cholinate according to the present invention; and
- to a pharmaceutical combination comprising said cholinate according to the present invention and one or more further pharmaceutical agents.

BACKGROUND OF THE PRESENT INVENTION 2-(1-cyclobutyl-1H-pyrazol-4-yl)-5-[({1-[2-fluoro-4-(trifluoromethyl)-phenyl]cyclopropyl}carbonyl)amino]benzoic acid is the compound of formula (I):

(I)

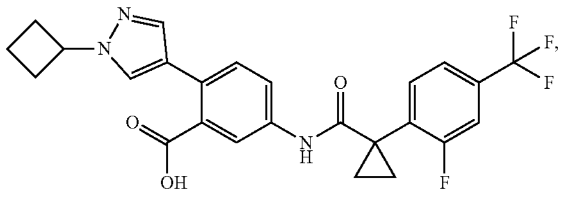

(which is hereinafter referred to as the "compound of formula (I)" or the "free acid"), which is a proprietary antagonist of the human Bradykinin B1 receptor (Gene Name BDKRB1, Gene ID 623; see Example 3 in International Patent Application No. WO 2018/114786 A1, filed on Dec. 18, 2017). The Bradykinin B1 receptor is a membrane-bound G-protein coupled receptor, which is linked to a second messenger system that triggers increase of intracellular calcium concentrations. The main signalling pathway is linked to Gq protein and phospholipase C (Leeb-Lundberg, L. M. et al. (2005), Pharmacol Rev 57(1): 27-77). The compound of formula (I) exhibits a broad spectrum of activity against Bradykinin B1 receptor related disorders and diseases, such as endometriosis, neuropathic pains, and overactive bladder, both in vitro and in vivo.

Said compound of formula (I) may be synthesised according to the methods given in international Patent Application WO 2018/114786 A1, filed on Dec. 18, 2017, (which is incorporated herein by reference in its entirety), e.g. on pp. 113 et seq., in particular as disclosed for Example 3 in WO 2018/114786 A1.

Experiments necessary for the pharmaceutical development include toxicological studies. To this end, it is a desirable to have good pharmacokinetic properties, i.e. bioavailability, over a wide dosage range in order to achieve sufficient exposure for the reliable toxicological testing within the organism. However, it was surprisingly found that the free acid does not show sufficient bioavailability at higher doses that would allow for further studies of the compound in terms of toxicity. Furthermore, during development of a compound for pharmaceutical applications it is desirable to provide for good pharmacokinetic properties, i.e. bioavailability, in order to reach a sufficient exposure in a patient to be treated. As such sufficient exposure, i.e. an exposure sufficient for ameliorating or curing the disease, is not known before the respective studies, it is desirable to provide the compound in a form that exhibits said good pharmacokinetic properties over a wide dosage range.

In an attempt to increase bioavailability of the compound by generating a salt, it turned out that the great majority of the tested salts were at least partially amorphous. For a salt being suited for pharmaceutical development it is desirable to have it in a crystalline form. Amorphous salts are difficult to handle as they are usually not free flowing under pharmaceutical processing conditions.

Accordingly, there is a need for a form of 2-(1-cyclobutyl-1H-pyrazol-4-yl)-5-[({1-[2-fluoro-4-(trifluoromethyl)-phenyl]cyclopropyl}carbonyl)amino]benzoic acid that provides sufficient bioavailability over a great dosage range and that has a crystalline form that may be used advantageously in pharmaceutical processing and pharmaceutical compositions and that is not hygroscopic.

SUMMARY OF THE INVENTION

The inventors surprisingly found that the cholinate of 2-(1-cyclobutyl-1H-pyrazol-4-yl)-5-[({1-[2-fluoro-4-(trifluoromethyl)-phenyl]cyclopropyl}carbonyl)amino]benzoic acid allows for both, a good bioavailability of the compound over a wide range of dose, i.e. also at higher doses, and a crystalline form.

Further, the inventors unexpectedly found that the cholinate according to the invention was the only salt that gave a completely crystalline form with reasonable efforts. As shown in the examples section herein, other salts than the cholinate according to the invention do either appear amorphous or only partially crystalline or with a yield far below any reasonable expectation.

Surprisingly, the cholinate, shows a higher solubility than the amorphous or partially crystalline salts.

Additionally, the cholinate according to the invention is less hygroscopic than the other salts, in particular also in the normal range of atmospheric relative humidity, which for example improves storage stability. Moreover, the crystalline cholinate salt not only dissolves faster than the free acid but also than the other salts of the compound, which were obtained in a partially crystalline or amorphous form.

Hence, the present invention not only solves the problem of providing a salt with the above outlined advantages but also provides a process for obtaining it in a time and yield suited fashion for industrial application.

Accordingly, the present invention relates to the cholinate of 2-(1-cyclobutyl-1H-pyrazol-4-yl)-5-[({1-[2-fluoro-4-(trifluoromethyl)-phenyl]cyclopropyl}carbonyl)amino]benzoic acid.

The terms "cholinate", "choline salt" and "2-hydroxy-N,N,N-trimethylethanaminium salt" are used interchangeably herein. They relate to a salt that has 2-hydroxy-N,N,N-trimethylethanaminium as a counterion.

Hence, in connection with the present invention, the terms "cholinate", "choline salt" and "2-hydroxy-N,N,N-trimethylethanaminium salt" "of 2-(1-cyclobutyl-1H-pyrazol-4-yl)-5-[({1-[2-fluoro-4-(trifluoromethyl)-phenyl]cyclopropyl}carbonyl)amino]benzoic acid", or "cholinate", "choline salt" and "2-hydroxy-N,N,N-trimethylethanaminium salt" "of the compound of formula (I)", as well as "cholinate according to the present invention", "choline salt according to the present invention" and "2-hydroxy-N,N,N-trimethylethanaminium salt according to the present invention", are used interchangeably herein and are meant to refer to "2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate".

Hence, the invention in particular relates to 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate.

In a particular embodiment of the invention 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate corresponds to formula (II):

(II)

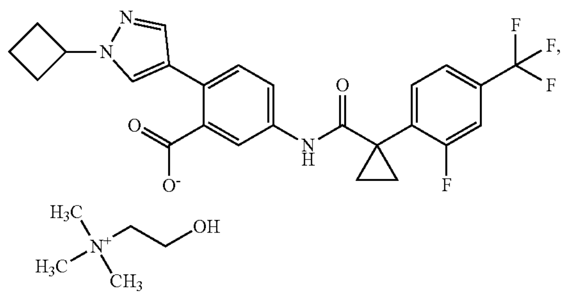

or a tautomer, solvate or hydrate thereof.

It has been found that the cholinate according to the present invention can—unlike other salts of the compound of formula (I)—be obtained in crystalline form in sufficient time, effort and yield and that it exhibits polymorphism/pseudopolymorphism.

Form A has been found to be the most stable form which is well suited for use in pharmaceutical applications. Hence, the present invention likewise relates to a crystalline form of the cholinate according to the present invention, preferably to a crystalline form of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate. Preferably the invention relates to polymorphic form A of the cholinate according to the present invention, to processes for its preparation, to pharmaceutical compositions comprising it and to its use in the control of disorders.

The following crystalline forms of the cholinate according to the invention have been identified which are polymorphic: form A and anhydrous form C, and mono 2-propanol solvate (form B) and a hexafluoro-2-propanol solvate (form D). In this context modifications, polymorphic forms and polymorphs have the same meaning. In addition the amorphous form exists. All together—the polymorphic forms, the pseudopolymorphic forms and the amorphous form—are different solid forms of the cholinate according to the invention.

Polymorphic form A of the crystalline cholinate according to the invention is thermodynamically stable at room temperature and at least up to 35° C.

Polymorphic form A is therefore suitable and preferred over the other solid or crystalline forms of the cholinate according to the invention for use in the pharmaceutical field, in particular suitable for pharmaceutical compositions.

In particular, polymorphic form A of the cholinate according to the present invention ensures that an undesired conversion into another form of the cholinate of the present invention and an associated change in the properties as described above is prevented. This increases the safety and quality of preparations and formulations comprising of the cholinate of the present invention and the risk to the patient is reduced.

The different crystalline forms of the cholinate according to the present invention can be distinguished by X-ray powder diffraction, differential scanning calorimetry (DSC), and IR-spectroscopy.

The polymorphic form A of the cholinate according to the invention can be characterized unambiguously by a X-Ray powder diffractogram (at 25° C. and with Cu—K alpha 1 as radiation source) which displays at least the following reflections: 12.99°, 20.42°, and 20.64°, preferably at least the following reflections: 12.99°, 20.42°, 20.64°, 18.84°, and 22.32°, more preferably at least the following reflections: 12.99°, 20.42°, 20.64°, 18.84°, 22.32°, 15.74°, and 20.75°, most preferably at least the following reflections: 12.99°, 20.42°, 20.64°, 18.84°, 22.32°, 15.74°, 20.75°, 24.42°, 17.62°, and 18.410; each quoted as 2Θ value±0.2°. The cholinate according to the invention in the polymorphic form A can also be characterized unambiguously by the X-Ray powder diffractogram (at 25° C. and with Cu—K alpha 1 as radiation source) as shown in FIG. 1.

Figure 2:
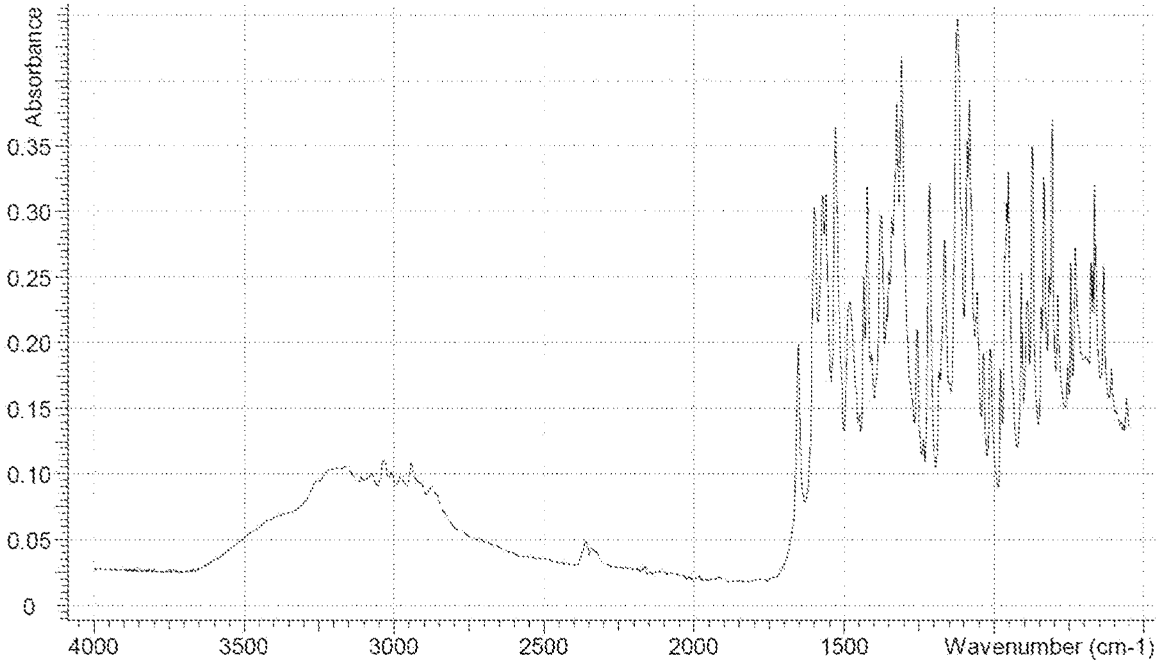

The polymorphic form A of the cholinate according to the invention can be unambiguously characterized by IR pattern (recorded at room temperature using a FT-IR-spectrophotometer using a Tensor 37 device from Bruker, with a resolution of 2 $cm^{-1}$) displaying at least the following bands, quoted as peak maxima in $cm^{-1}$: 1123, 1309, and 1083; preferably displaying at least the following bands, quoted as peak maxima in $cm^{-1}$: 1123, 1309, 1083, 1324, and 808; more preferably displaying at least the following bands, quoted as peak maxima in $cm^{-1}$: 1123, 1309, 1083, 1324, 808, 1091, and 874; most preferably displaying at least the following bands, quoted as peak maxima in $cm^{-1}$: 1123, 1309, 1083, 1324, 808, 1091, 874, 1530, 954, and 835. The cholinate according to the invention in the polymorphic form A can also be characterized unambiguously by the IR pattern (recorded at room temperature using a FT-IR-spectrophotometer using a Tensor 37 device from Bruker, with a resolution of 2 $cm^{-1}$) as shown in FIG. 2.

Method for Preparing the Cholinate According to the Invention

Further, the present invention relates to a method of preparing 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate (also referred to as the cholinate according to the invention), said method comprising the step of adding 2-hydroxy-N, N, N-trimethylethanaminium hydroxide to 2-(1-cyclobutyl-1H-pyrazol-4-yl)-5-[({1-[2-fluoro-4-(trifluoromethyl)-phenyl] cyclopropyl}carbonyl)amino]benzoic acid in a suitable solvent, preferably toluene, ethanol, acetonitrile or mixtures thereof, preferably a mixture of ethanol and acetonitrile, preferably a mixture of ethanol and acetonitrile (7:100), thereby forming said cholinate of the compound of formula (I). The cholinate according to the invention can be separated as a solid at this stage by filtering and/or drying.

The invention further relates to a method of preparing the cholinate according to the invention in a crystalline form, preferably in crystalline Form A, comprising dissolving the obtained solid in a suitable solvent, such as, for example, a solvent selected from the group consisting of acetonitrile, ethanol, methyl tert-butyl ether, ethyl acetate, heptane, toluene, tetrahydrofuran, butanol, acetone, water and mixtures thereof, at a suitable temperature, followed by cooling the solution to a temperature allowing precipitation of salt crystals, preferably cooling to 4° C. (+/−2° C.).

In a particular embodiment the method of preparing the cholinate according to the invention comprises adding to the compound of formula (I):

(I)

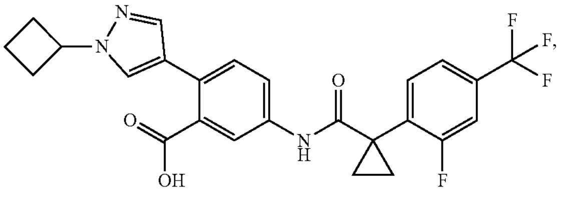

the compound of formula (III):

(III)

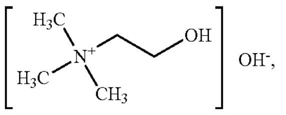

thereby forming 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate according to formula (II):

(II)

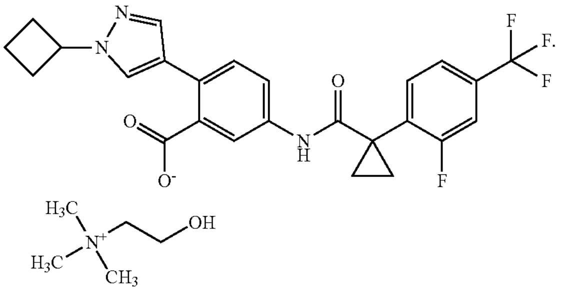

In a preferred embodiment said method comprises adding to a suspension of the compound of formula (I):

(I)

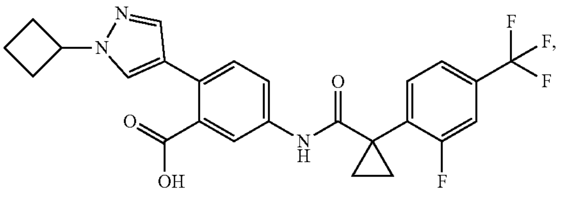

a compound of formula (III):

(III)

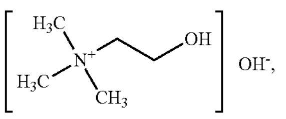

thereby forming said cholinate according to formula (II):

(II)

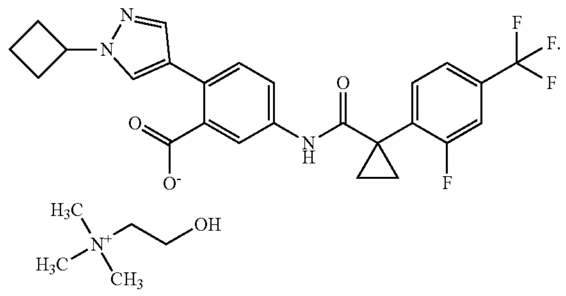

The combination of the compounds of formulae (I) and (III) may be conducted in a suited medium. Suited media may be selected by the skilled person, preferably it is an alcohol, preferably a $C_1$-$C_4$ alcohol, most preferred tert-butanol or iso-butanol (2-methylpropan-1-ol).

Preferably, the addition step comprises mixing of the compounds of formulae (I) and (III) to obtain the cholinate according to the invention.

Further, the skilled person may choose suited conditions for the addition and/or mixing, e.g. as regards the temperature. Preferably, the temperature for the addition of said compounds is between the freezing point of the mixture and the boiling point of the mixture, more preferably it is at room temperature, such as for example 22° C. (+/−20).

In a preferred embodiment the obtained mixture is stirred at a temperature of between the freezing point of the mixture and the boiling point of the mixture, preferably at room temperature, such as at 22° C. (+/−2°) for example, for a period of time, such as for 1 to 48 hours, preferably 12 to 36 hours, more preferably 14 to 20 hours, such as for 18 hours.

In a further preferred embodiment, the cholinate according to the invention as obtained may be dried. Preferably by evaporating the solvents. If deemed necessary, the obtained cholinate according to the invention can be washed once or twice. The washing solvents may be chosen by those skilled in the art and are preferably water-immiscible. Preferably, the obtained cholinate salt is washed once or twice with toluene.

It may be desirable to (re)crystallize the obtained solid cholinate according to the invention, in particular for obtaining Form A. Hence, in a preferred embodiment the method for preparing the cholinate according to the present invention, preferably in a crystalline form, more preferably in Form A, further comprises the steps of:

- dissolving the obtained solid in a solvent, such as for example a solvent selected from the group consisting of acetonitrile, ethanol, methyl tert-butyl ether, ethyl acetate, heptane, toluene, tetrahydrofuran, butanol, acetone, water and mixtures thereof, by stirring over a period of time at a temperature sufficient for the solid to dissolve,
- cooling the solution with stirring to a temperature allowing the precipitation of salt crystals, such as 4° C. (+/−2° C.); and, optionally
  - further stirring at a temperature of 4° C. (+/−2° C.) for a period of time, for example 1 hour, and optionally filtering off the resulting cholinate of 2-(1-cyclobutyl-1H-pyrazol-4-yl)-5-[({1-[2-fluoro-4-(trifluoromethyl)-phenyl]cyclopropyl}carbonyl)amino]benzoic acid, optionally washing with acetonitrile, ethanol, methyl tert-butyl ether, ethyl acetate, heptane, toluene, tetrahydrofuran, butanol, acetone, or water or a mixture thereof; preferably washing with the solvent used for dissolving the initial solid, and optionally drying, for example under reduced pressure (e.g. 200 mbar) at a temperature between 20° C. and 60° C. for example; thus providing crystalline 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate of form A.

The skilled person is aware of methods for providing the compound of formula (I). In particular, methods for the synthesis of 2-(1-cyclobutyl-1H-pyrazol-4-yl)-5-[({1-[2-fluoro-4-(trifluoromethyl)phenyl]cyclopropyl}carbonyl)amino]benzoic acid are disclosed in Example 3 in WO 2018/114786 A1 (incorporated herein by reference).

The skilled person further is able to adapt the methods for synthesizing 2-(1-cyclobutyl-1H-pyrazol-4-yl)-5-[({1-[2-fluoro-4-(trifluoromethyl)phenyl]cyclopropyl}carbonyl)amino]benzoic acid as disclosed in Example 3 in WO 2018/114786 A1. For example, one may choose to exchange the reactivity of the nucleophile and electrophile in the Suzuki cross-coupling reaction by changing the boronic ester group to the bromide group of one adduct and changing the bromide group to the boronic ester group of the other adduct as compared to the disclosed for "Intermediate 29A" in WO 2018/114786 A1. A respective alternative way is disclosed in the Example section herein below.

Pharmaceutical Compositions

The present invention also relates to a pharmaceutical composition comprising the cholinate according to the present invention. In particular the present invention relates to a pharmaceutical composition comprising 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate, preferably a crystalline form thereof (more preferably form A), and optionally one or more pharmaceutically acceptable excipients.

A preferred pharmaceutical composition according to the present invention comprises cholinate according to formula (II) and optionally one or more further pharmaceutically acceptable excipient.

A preferred embodiment of the present invention is a pharmaceutical composition comprising polymorphic form A of the cholinate according to formula (II), further preferred is a composition which comprises form A of the cholinate according to formula (II) mainly and no significant fractions of another form of the cholinate according to formula (II) and optionally one or more further pharmaceutically acceptable excipients. More preferably the pharmaceutical composition contains more than 85 percent by weight, more preferably more than 90 percent by weight, most preferably more than 95 percent by weight, of the polymorphic form A of the cholinate according to formula (II) related to the total amount of all forms of the cholinate according to formula (II) present in the composition.

It is possible for the cholinate according to the invention to have systemic and/or local activity. For this purpose, it can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the cholinate according to the invention to be administered in suitable administration forms.

For oral administration, which is preferred, it is possible to formulate the cholinate according to the invention to dosage forms known in the art that deliver the compound of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the cholinate according to the invention in crystalline and/or amorphised and/or dissolved form into said dosage forms, preferably in crystalline form. Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The cholinate according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropyl, cellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropyl, methylcellulose phthalate, cellulose acetate, cellulose acetate phthalate, polyacrylates, polymethacrylates such as, for example, Eudragit®)),
- capsule materials (for example gelatine, hydroxypropylmethylcellulose),
- synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
- plasticizers (for example polyethylene glycols, propylene glycol, glycerol, triacetine, triacetyl citrate, dibutyl phthalate),
- penetration enhancers,
- stabilisers (for example antioxidants such as, for example, ascorbic acid, ascorbyl palmitate, sodium ascorbate, butylhydroxyanisole, butylhydroxytoluene, propyl gallate),
- preservatives (for example parabens, sorbic acid, thiomersal, benzalkonium chloride, chlorhexidine acetate, sodium benzoate),
- colourants (for example inorganic pigments such as, for example, iron oxides, titanium dioxide),
- flavourings, sweeteners, flavour- and/or odour-masking agents.

The present invention furthermore relates to pharmaceutical compositions which comprise the cholinate according to the invention, conventionally together with one or more pharmaceutically suitable excipient(s), and to their use according to the present invention.

Methods of Treating

The present invention relates to a method for using the cholinate according to the present invention and compositions thereof, to inhibit the Bradykinin B1 receptor. The present invention relates to a method for using the choline salt of the present invention and compositions thereof, to treat mammalian disorders and diseases which include but are not limited to:

Diseases related to pain and/or inflammation, in particular selected from the group consisting of

- visceral pain e.g. related to pancreatitis, interstitial cystitis, renal colic, or prostatitis, chronic pelvic pain, or pain related to infiltrating endometriosis;
- neuropathic pain such as post herpetic neuralgia, acute zoster pain, pain related to nerve injury, the dynias, including vulvodynia, phantom limb pain, pain related to root avulsions, pain related to radiculopathy, painful traumatic mononeuropathy, painful entrapment neuropathy, pain related to carpal tunnel syndrome, ulnar neuropathy, pain related to tarsal tunnel syndrome, painful diabetic neuropathy, diabetic neuropathic pain, painful polyneuropathy, trigeminal neuralgia, or pain related to familial amyloid polyneuropathy;

central pain syndromes potentially caused by virtually any lesion at any level of the nervous system including but not limited to pain related to stroke, multiple sclerosis, and spinal cord injury;

postsurgical pain syndromes (including postmastectomy pain syndrome, postthoracotomy pain syndrome, stump pain), bone and joint pain (osteoarthritis), spine pain (including acute and chronic low back pain, neck pain, pain related to spinal stenosis), shoulder pain, repetitive motion pain, dental pain, pain related to sore throat, cancer pain, burn pain including sun-burn, myofascial pain (pain related to muscular injury, fibromyalgia) postoperative, and perioperative pain (including but not limited to general surgery, orthopaedic, and gynaecological surgery); and acute and chronic pain, chronic pelvic pain, endometriosis associated pain, dysmenorrhea associated pain (primary and secondary), painassociated with uterine fibroids, vulvodynia associated pain, as well as pain associated with angina, Bladder Pain Syndrome, or inflammatory pain of varied origins (including but not limited to pain associated with osteoarthritis, rheumatoid arthritis, rheumatic disease, tenosynovitis, gout, ankylosing spondylitis, and bursitis); and diseases like or related to a disease selected from related to the group consisting of:

gynaecological disorders and/or diseases, or effects and/or symptoms which negatively influence women health including endometriosis, uterine fibroids, pre-eclampsia, hormonal deficiency, spasms of the uterus, or heavy menstrual bleeding;

the respiratory or excretion system including any of inflammatory hyperreactive airways, inflammatory events associated with airways disease like chronic obstructive pulmonary disease, asthma including allergic asthma (atopic or non-atopic) as well as exercise-induced bronchoconstriction, occupational asthma, viral or bacterial exacerbation of asthma, other non-allergic asthmas and wheezy-infant syndrome, chronic obstructive pulmonary disease including emphysema, adult respiratory distress syndrome, bronchitis, pneumonia, cough, lung injury, lung fibrosis, allergic rhinitis (seasonal and perennial), vasomotor rhinitis, angioedema (including hereditary angioedema and drug-induced angioedema including that caused by angiotensin converting enzyme (ACE) or ACE/neutral endopeptidase inhibitors like omepatrilat), pneumoconiosis, including aluminosis, anthracosis, asbestosis, chalicosis, ptilosis, siderosis, silicosis, tabacosis and byssinosis, bowel disease including Crohn's disease and ulcerative colitis, irritable bowel syndrome, pancreatitis, nephritis, cystitis (interstitial cystitis), kidney fibrosis, kidney failure, hyperactive bladder, and overactive bladder;

dermatology including pruritus, itch, inflammatory skin disorders including psoriasis, eczema, and atopic dermatitis;

affection of the joints or bones including rheumatoid arthritis, gout, osteoporosis, osteoarthritis, and ankylosing spondylitis;

affection of the central and peripheral nervous system including neurodegenerative diseases including Parkinson's and Alzheimer's disease, amyotrophic lateral sclerosis (ALS), epilepsy, dementia, headache including cluster headache, migraine including prophylactic and acute use, stroke, closed head trauma, and multiple sclerosis;

infection including HIV infection, and tuberculosis;

trauma associated with oedema including cerebral oedema, burns, sunburns, and sprains or fracture;

poisoning including aluminosis, anthracosis, asbestosis, chalicosis, ptilosis, siderosis, silicosis, tabacosis, and byssinosis uveitis;

diabetes cluster or metabolism like diabetes type 1, diabetes type 2, diabetic vasculopathy, diabetic neuropathy, diabetic retinopathy, post capillary resistance or diabetic symptoms associated with insulitis (e.g. hyperglycaemia, diuresis, proteinuria and increased nitrite and kallikrein urinary excretion), diabetic macular oedema, metabolic syndrome, insulin resistance, obesity, or fat or muscle metabolism;

cachexia associated with or induced by any of cancer, AIDS, coeliac disease, chronic obstructive pulmonary disease, multiple sclerosis, rheumatoid arthritis, congestive heart failure, tuberculosis, familial amyloid polyneuropathy, mercury poisoning (acrodynia), and hormonal deficiency;

cardio-vascular system including congestive heart failure, atherosclerosis, congestive heart failure, myocardial infarct, and heart fibrosis; and other conditions including septic shock, sepsis, muscle atrophy, spasms of the gastrointestinal tract, benign prostatic hyperplasia, and liver diseases such as non-alcoholic and alcoholic fatty liver disease, non alcoholic and alcoholic steatohepatitis, liver fibrosis, or liver cirrhosis.

A preferred embodiment of the present invention relates to a method for using the cholinate or compositions thereof according to the present invention, to treat a gynaecological disease, preferably endometriosis, endometriosis-associated pain, or other endometriosis-associated symptoms; diabetic neuropathic pain, interstitial cystitis and bladder pain syndrome [also referred to as interstitial cystitis/bladder pain syndrome (IC/BPS), and endometriosis.

Further preferred is a method for using the cholinate or compositions thereof according to the present invention for the treatment of a disease selected from the group consisting of diabetic neuropathic pain, interstitial cystitis, bladder pain syndrome, and endometriosis. In a particular preferred embodiment the invention relates to a method for using the cholinate according to the present invention or compositions comprising the cholinate according to the invention for the treatment of a disease selected from the group consisting of diabetic neuropathic pain, interstitial cystitis, bladder pain syndrome, and endometriosis.

Additionally the present invention relates to a method for using the compound of the present invention and compositions thereof, to treat osteoarthritis, rheumatoid arthritis, gout, neuropathic pain, diabetic neuropathic pain, asthma, cough, lung injury, lung fibrosis, pneumonia, kidney fibrosis, kidney failure pruritus, irritable bowel disease, overactive urinary bladder, diabetes type 1, diabetes type 2, diabetic neuropathy, diabetic retinopathy, diabetic macular oedema, metabolic syndrome, obesity, heart fibrosis, cachexia, muscle atrophy, Alzheimer's disease, Bladder Pain Syndrome, and interstitial cystitis.

In a particular preferred embodiment, the present invention relates to a method for using 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate or a composition comprising the same for the treatment of a disease, preferably a disease related to pain and/or inflammation. Hence, the invention also relates to 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate or a composition comprising the same for use in the treatment of a disease, preferably a disease related to pain and/or inflammation These disorders have been well characterized in humans, but also exist with a similar etiology in other mammals, and can be treated by administering the cholinate or pharmaceutical compositions of the present invention. The term "treating" or "treatment" as stated throughout this document is used conventionally, e.g., the management or care of a subject for the purpose of combating, alleviating, reducing, relieving, improving the condition of, etc., of a disease or disorder, such as a gynaecological disease.

Dose and Administration

Based upon standard laboratory techniques known to evaluate compounds useful for the treatment of disorders and/or diseases which are mediated by Bradykinin B1 receptor, by standard toxicity tests and by standard pharmacological assays for the determination of treatment of the conditions identified above in mammals, and by comparison of these results with the results of known medicaments that are used to treat these conditions, the effective dosage of the cholinate according to the invention can readily be determined for treatment of each desired indication. The amount of the active ingredient to be administered in the treatment of one of these conditions can vary widely according to such considerations as the dosage unit employed the mode of administration, the period of treatment, the age and sex of the patient treated, and the nature and extent of the condition treated.

The skilled person will acknowledge that for the dosage the administered amount of the pharmaceutically active compound is detrimental. The cholinate according to the present invention is a salt of an active pharmaceutically compound, i.e. 2-(1-cyclobutyl-1H-pyrazol-4-yl)-5-[({1-[2-fluoro-4-(trifluoromethyl)-phenyl]cyclopropyl}carbonyl)amino]benzoic acid. 2-(1-cyclobutyl-1H-pyrazol-4-yl)-5-[({1-[2-fluoro-4-(trifluoromethyl)-phenyl]cyclopropyl}carbonyl)amino]benzoic acid (also referred to as the "active ingredient"). Accordingly, the doses are preferably referring to the amount of this free acid being administered. The total amount of the active ingredient to be administered will generally range as to deliver from about 0.001 mg/kg to about 100 mg/kg body weight per day of the free acid, preferably from about 0.01 mg/kg to about 20 mg/kg body weight per day. A preferred administration of the compound of the present invention includes but is not limited to 0.1 mg/kg to about 10 mg/kg body weight per day. Clinically useful dosing schedules will range from one to three times a day dosing to once every four weeks dosing.

In addition, "drug holidays" in which a patient is not dosed with a drug for a certain period of time, may be beneficial to the overall balance between pharmacological effect and tolerability.

A total daily dosage may range from about 0.5 mg to about 2000 mg of active ingredient, and can be administered one or more times per day or less than once a day.

The cholinate according to the present invention provided for a surprisingly good bioavailability for the active ingredient in particular when administered orally. Accordingly, the dosage form is preferably an oral dosage form.

The preferred daily dosage of the active ingredient is ranging from 0.5 mg to 2000 mg, preferably 100 mg to 1600 mg, such as 100 mg, 150 mg, 200 mg, 400 mg, 450 mg, 600 mg, 800 mg, and 1600 mg.

The skilled person will recognize that for achieving such dosage of the active ingredient a dosage of the cholinate according to the present invention is to be used that takes into account the mass the choline salt is adding. For providing a dosage of for example 1 mg of the active ingredient a dosage of about 1.2 mg (such as from 1.20 mg to 1.25 mg, or 1.21 mg or 1.24 mg) of the cholinate according to the invention is to be used, i.e. the about 1.2 fold (such as from 1.20 to 1.25 fold, or 1.209 fold or 1.24 fold) of the respective amount.

Hence, in a preferred embodiment the daily dosage of the cholinate according to the present invention is from about 0.6 mg to about 2480 mg, preferably from about 124 mg to about 1984 mg, such as a daily dose of about 124 mg, about 186 mg, about 248 mg, about 496 mg, about 558 mg, about 744 mg, about 992 mg, and about 1984 mg of the cholinate according to the invention. The term "about" refers to amounts acceptable for pharmaceutical application, preferably within a range of +/−10% or +/−5% of the respective amount/dosage given, preferably within a range of −10% and +5%.

The desired daily dosage may be reached by administering a single dosage unit a day that comprises the amount of the desired daily dosage or by administering of single dosage units comprising a portion of the desired daily dosage in a number to sum up to the desired daily dosage. For example, to administer a daily dosage of 150 mg, a single dosage unit comprising 150 mg of the active ingredient, or three single dosage units with each comprising 50 mg of the active ingredient may be administered.

The amount of active ingredient within a single dosage unit may vary depending on the desired daily dosage. Preferably a single dosage unit comprises 10 mg to 1600 mg of the active ingredient (or from about 12.4 mg to about 1984 mg of the cholinate according to the present invention), preferably 50 mg to 450 mg of the active ingredient, more preferably 50 mg to 150 mg of the active ingredient (about 62 mg to about 186 mg of the cholinate according to the present invention). In a particular preferred embodiment a single dosage unit comprises 50 mg or 150 mg of the active ingredient (about 62 mg or a bit 186 mg of the cholinate according to the present invention).

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of cholinate according to the invention or composition thereof can be ascertained by those skilled in the art using conventional treatment tests.

Combination Therapies

The term "combination" in the present invention is used as known to persons skilled in the art and may be present as a fixed combination, a non fixed combination or kit of parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non fixed combination or "kit of parts" in the present invention is used as known to persons skilled in the art and is defined as a combination wherein the said first active ingredient and the said second active ingredient are present in more than one unit. One example of a non fixed combination or kit of parts is a combination wherein the said first active ingredient and the said second active ingredient are present separately. The components of the non fixed combination or kit of parts may be administered separately, sequentially, simultaneously, concurrently or chronologically staggered.

The cholinate according to the present invention can be administered as the sole pharmaceutical agent or in combination with one or more other pharmaceutical agents where the combination causes no unacceptable adverse effects. The present invention relates also to such combinations.

The cholinate according to the present invention can be combined with therapeutic agents or active ingredients, that are already approved or that are still under development for the treatment and/or prophylaxis of diseases which are related to or mediated by the Bradykinin B1 receptor.

For the treatment and/or prophylaxis of urinary tract diseases, the cholinate according to the present invention can be administered in combination or as co-medication with any substance that can be applied as therapeutic agent in the following indications:

Urinary tract disease states associated with the bladder outlet obstruction; urinary incontinence conditions such as reduced bladder capacity, increased frequency of micturition, urge incontinence, stress incontinence, or bladder hyperreactivity; benign prostatic hypertrophy; prostatic hyperplasia; prostatitis; detrusor hyperreflexia; overactive bladder and symptoms related to overactive bladder wherein said symptoms are in particular increased urinary frequency, nocturia, urinary urgency or urge incontinence; pelvic hypersensitivity; urethritis; prostatitis; prostatodynia; cystitis, in particular interstitial cystitis/bladder pain syndrome (IC/BPS); idiopathic bladder hypersensitivity.

For the treatment and/or prophylaxis of overactive bladder and symptoms related to overactive bladder, the compounds of the present invention can be administered in combination or as co-medication in addition to behavioural therapy like diet, lifestyle or bladder training with anticholinergics like oxybutynin, tolterodine, propiverine, solifenacin, darifenacin, trospium, fesoterdine; ß-3 agonists like mirabegron; neurotoxins like onabutolinumtoxin A; or antidepressants like imipramine, duloxetine. For the treatment and/or prophylaxis of interstitial cystitis, the compounds of the present invention can be administered in combination or as co-medication in addition to behavioural therapy like diet, lifestyle or bladder training with pentosans like elmiron; antidepressants like amitriptyline, imipramine; or antihistamines like loratadine.

For the treatment and/or prophylaxis of gynaecological diseases, the compounds of the present invention can be administered in combination or as co-medication with any substance that can be applied as therapeutic agent in the following indications:

dysmenorrhea, including primary and secondary; dyspareunia; endometriosis; endometriosis-associated pain; endometriosis-associated symptoms, such as and in particular dysmenorrhea, dyspareunia, dysuria, or dyschezia.

For the treatment and/or prophylaxis of dysmenorrhea, including primary and secondary; dyspareunia; endometriosis and endometriosis-associated pain, the compounds of the present invention can be administered in in combination with ovulation inhibiting treatment, in particular COCs as mentioned above or contraceptive patches like Ortho-Evra or Apleek (Lisvy); or with progestogenes like dienogest (Visanne); or with GnRH analogous, in particular GnRH agonists and antagonists, for example leuprorelin, nafarelin, goserelin, cetrorelix, abarelix, ganirelix, degarelix; or with androgens: danazol.

For the treatment and/or prophylaxis of diseases, which are associated with pain, or pain syndromes, the cholinate according to the present invention can be administered in combination or as co-medication with any substance that can be applied as therapeutic agent in the following indications:

pain-associated diseases or disorders like hyperalgesia, allodynia, functional bowel disorders (such as irritable bowel syndrome) and arthritis (such as osteoarthritis, rheumatoid arthritis and ankylosing spondylitis), burning mouth syndrome, burns, migraine or cluster headache, nerve injury, traumatic nerve injury, post-traumatic injuries (including fractures and sport injuries), neuritis, neuralgia, poisoning, ischemic injury, interstitial cystitis, viral, trigeminal neuralgia, small fiber neuropathy, diabetic neuropathy, diabetic neuropathic pain, chronic arthritis and related neuralgias, HIV and HIV treatment-induced neuropathy.

The cholinate according to the present invention can be combined with other pharmacological agents and compounds that are intended to treat inflammatory diseases, inflammatory pain or general pain conditions.

In addition to well-known medicaments which are already approved and on the market, the cholinate according to the present invention can be administered in combination with inhibitors of the P2X purinoceptor family (P2X3, P2X4), with inhibitors of IRAK4 and with antagonists of the prostanoid EP4 receptor.

In particular, the cholinate according to the present invention can be administered in combination with pharmacological endometriosis agents, intended to treat inflammatory diseases, inflammatory pain or general pain conditions and/or interfering with endometriotic proliferation and endometriosis associated symptoms, namely with inhibitors of Aldo-keto-reductase1C3 (AKR1C3) and with functional blocking antibodies of the prolactin receptor.

The cholinate according to the present invention can be combined with other pharmacological agents and compounds that are intended for the treatment, prevention or management of cancer.

In particular, the cholinate according to the present invention can be administered in combination with 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, or zorubicin.

Furthermore, the cholinate according to the present invention can be combined with active ingredients, which are well known for the treatment of cancer-related pain and chronic pain. Such combinations include, but are not limited to step II opioids like codeine phosphate, dextropropoxyphene, dihydro-codeine, Tramadol), step III opioids like morphine, fentanyl, buprenorphine, oxymorphone, oxycodone and hydromorphone; and other medications used for the treatment of cancer pain like steroids as Dexamethasone and methylprednisolone; bisphosphonates like Etidronate, Clodronate, Alendronate, Risedronate, and Zoledronate; tricyclic antidepressants like Amitriptyline, Clomipramine, Desipramine, Imipramine and Doxepin; class I antiarrhythmics like mexiletine and lidocaine; anticonvulsants like carbamazepine, Gabapentin, oxcarbazepine, phenytoin, pregabalin, topiramate, alprazolam, diazepam, flurazepam, pentobarbital and phenobarbital.

In addition to those mentioned above, the inventive cholinate according to the invention can also be combined with any of the following active ingredients:

active ingredients for Alzheimer's therapy, for example acetylcholinesterase inhibitors (e.g. donepezil, rivastigmine, galantamine, tacrine), NMDA (N-methyl-D-aspartate) receptor antagonists (e.g. memantine); L-DOPA/carbidopa (L-3,4-dihydroxyphenylalanine), COMT (catechol-O-methyltransferase) inhibitors (e.g. entacapone), dopamine agonists (e.g. ropinrole, pramipexole, bromocriptine), MAO-B (monoaminooxidase-B) inhibitors (e.g. selegiline), anticholinergics (e.g. trihexyphenidyl) and NMDA antagonists (e.g. amantadine) for treatment of Parkinson's; beta-interferon (IFN-beta) (e.g. IFN beta-1b, IFN beta-1a Avonex® and Betaferon®), glatiramer acetate, immunoglobulins, natalizumab, fingolimod and immunosuppressants such as mitoxantrone, azathioprine and cyclophosphamide for treatment of multiple sclerosis; substances for treatment of pulmonary disorders, for example beta-2-sympathomimetics (e.g. salbutamol), anticholinergics (e.g. glycopyrronium), methylxanthines (e.g. theophylline), leukotriene receptor antagonists (e.g. montelukast), PDE-4 (phosphodiesterase type 4) inhibitors (e.g. roflumilast), methotrexate, IgE antibodies, azathioprine and cyclophosphamide, cortisol-containing preparations; substances for treatment of osteoarthritis such as non-steroidal anti-inflammatory substances (NSAIDs). In addition to the two therapies mentioned, methotrexate and biologics for B-cell and T-cell therapy (e.g. rituximab, abatacept) should be mentioned for rheumatoid disorders such as rheumatoid arthritis and juvenile idiopathic arthritis. Neurotrophic substances such as acetylcholinesterase inhibitors (e.g. donepezil), MAO (monoaminooxidase) inhibitors (e.g. selegiline), interferons und anticonvulsives (e.g. gabapentin); active ingredients for treatment of cardiovascular disorders such as beta-blockers (e.g. metoprolol), ACE inhibitors (e.g. benazepril), diuretics (e.g. hydrochlorothiazide), calcium channel blockers (e.g. nifedipine), statins (e.g. simvastatin); anti-diabetic drugs, for example metformin and glibenclamide, sulphonylureas (e.g. tolbutamide) and insulin therapy for treatment of diabetes and metabolic syndrome. Active ingredients such as mesalazine, sulfasalazine, azathioprine, 6-mercaptopurine or methotrexate, probiotic bacteria (Mutaflor, VSL #3®, *Lactobacillus* GG, *Lactobacillus plantarum, L. acidophilus, L. casei, Bifidobacterium infantis* 35624, *Enterococcus fecium* SF68, *Bifidobacterium longum, Escherichia coli* Nissle 1917), antibiotics, for example ciprofloxacin and metronidazole, anti-diarrhoea drugs, for example loperamide, or laxatives (bisacodyl) for treatment of chronic-inflammatory bowel disorders. Immunosuppressants such as glucocorticoids and non-steroidale anti-inflammatory substances (NSAIDs), cortisone, chloroquine, cyclosporine, azathioprine, belimumab, rituximab, cyclophosphamide for treatment of lupus erythematosus. By way of example but not exclusively, calcineurin inhibitors (e.g. tacrolimus and ciclosporin), cell division inhibitors (e.g. azathioprine, mycophenolate mofetil, mycophenolic acid, everolimus or sirolimus), rapamycin, basiliximab, daclizumab, anti-CD3 antibodies, anti-T-lymphocyte globulin/anti-lymphocyte globulin for organ transplants, Vitamin D3 analogues, for example calcipotriol, tacalcitol or calcitriol, salicylic acid, urea, ciclosporine, methotrexate, or efalizumab for dermatological disorders.

The invention is further examplified by the following Figures and Examples, which are not to be taken as limiting the invention, but are only of illustrative nature.

FIGURE LEGEND

Figure 3:
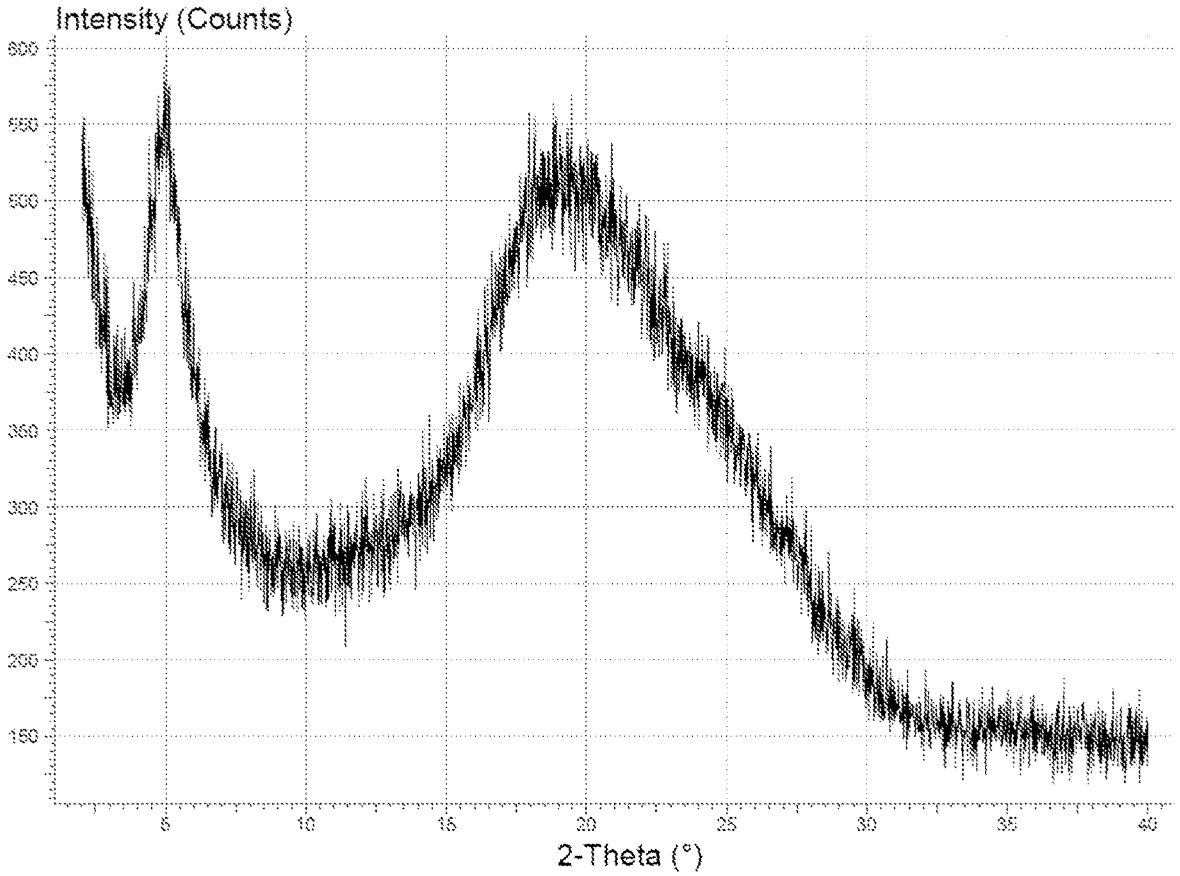
Figure 5:
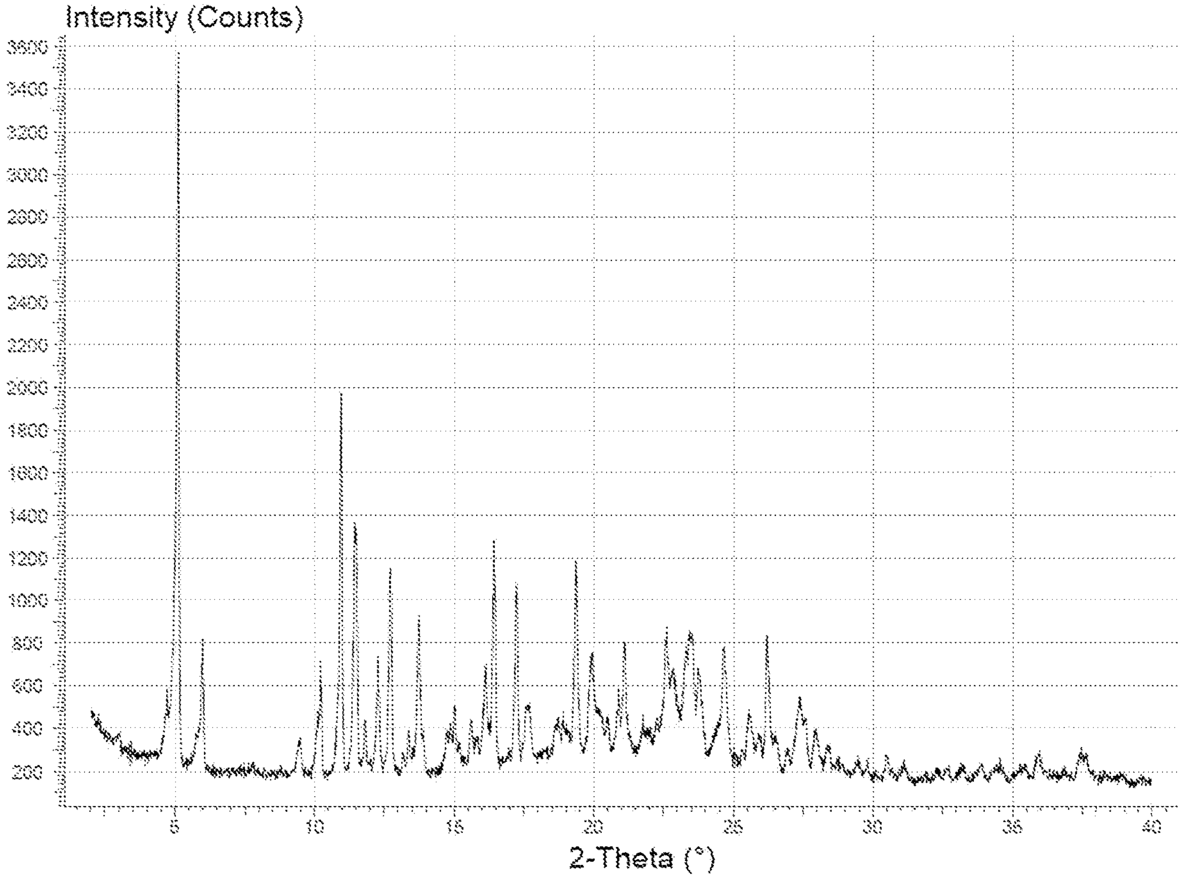
Figure 6:
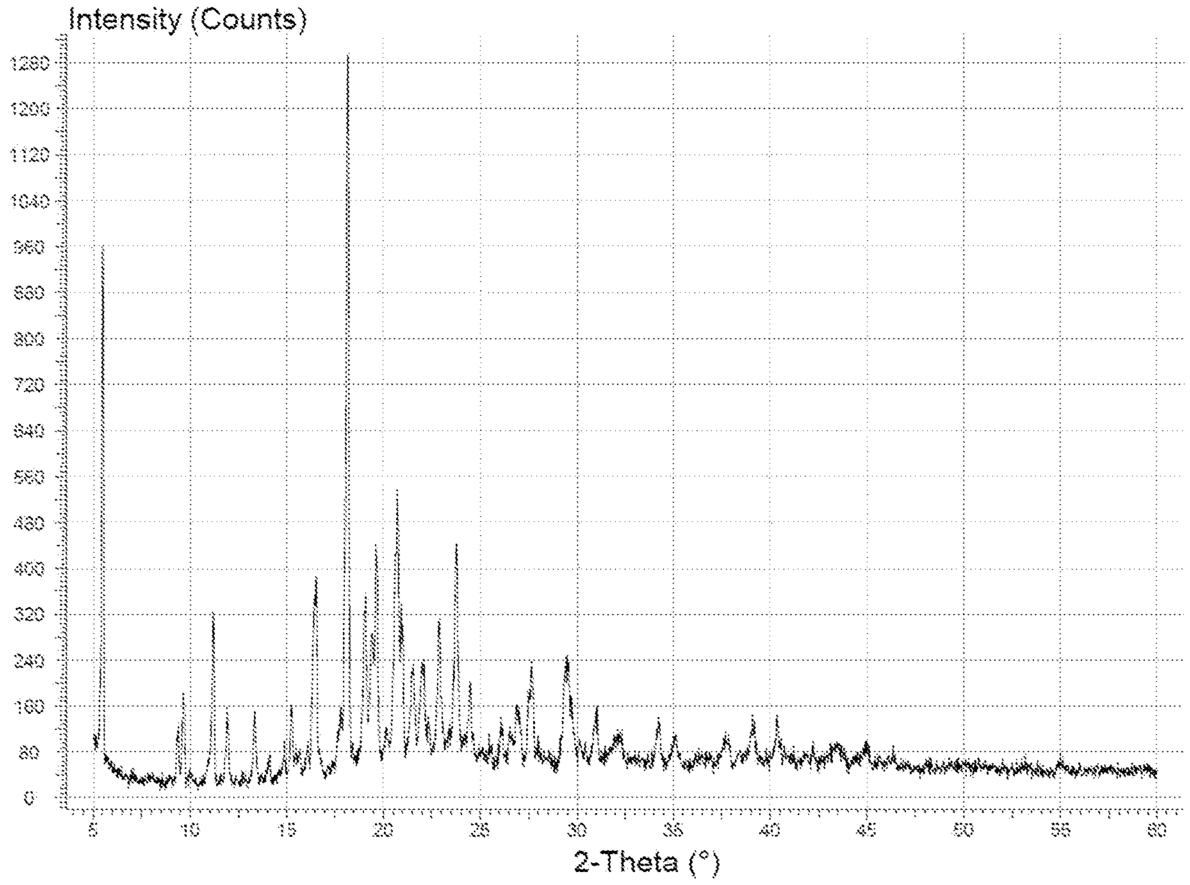

FIG. 1: XRPD pattern of polymorphic form A of the cholinate according to the invention FIG. 2: FT-IR spectrum of polymorphic form A of the cholinate according to the invention FIG. 3: XRPD pattern of amorphous sodium 2-(1-cyclobutyl-1H-pyrazol-4-yl)-5-[({1-[2-fluoro-4-(trifluoromethyl) phenyl]cyclopropyl}carbonyl)amino]benzoate FIG. 4: XRPD pattern of partially crystalline sodium 2-(1-cyclobutyl-1H-pyrazol-4-yl)-5-[({1-[2-fluoro-4-(trifluoromethyl) phenyl]cyclopropyl}carbonyl)amino]benzoate FIG. 5: XRPD pattern of crystalline sodium 2-(1-cyclobutyl-1H-pyrazol-4-yl)-5-[({1-[2-fluoro-4-(trifluoromethyl) phenyl]cyclopropyl}carbonyl)amino]benzoate FIG. 6: XRPD pattern of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl) amino]benzoate mono 2-propanol solvate (form B)

Figure 7:
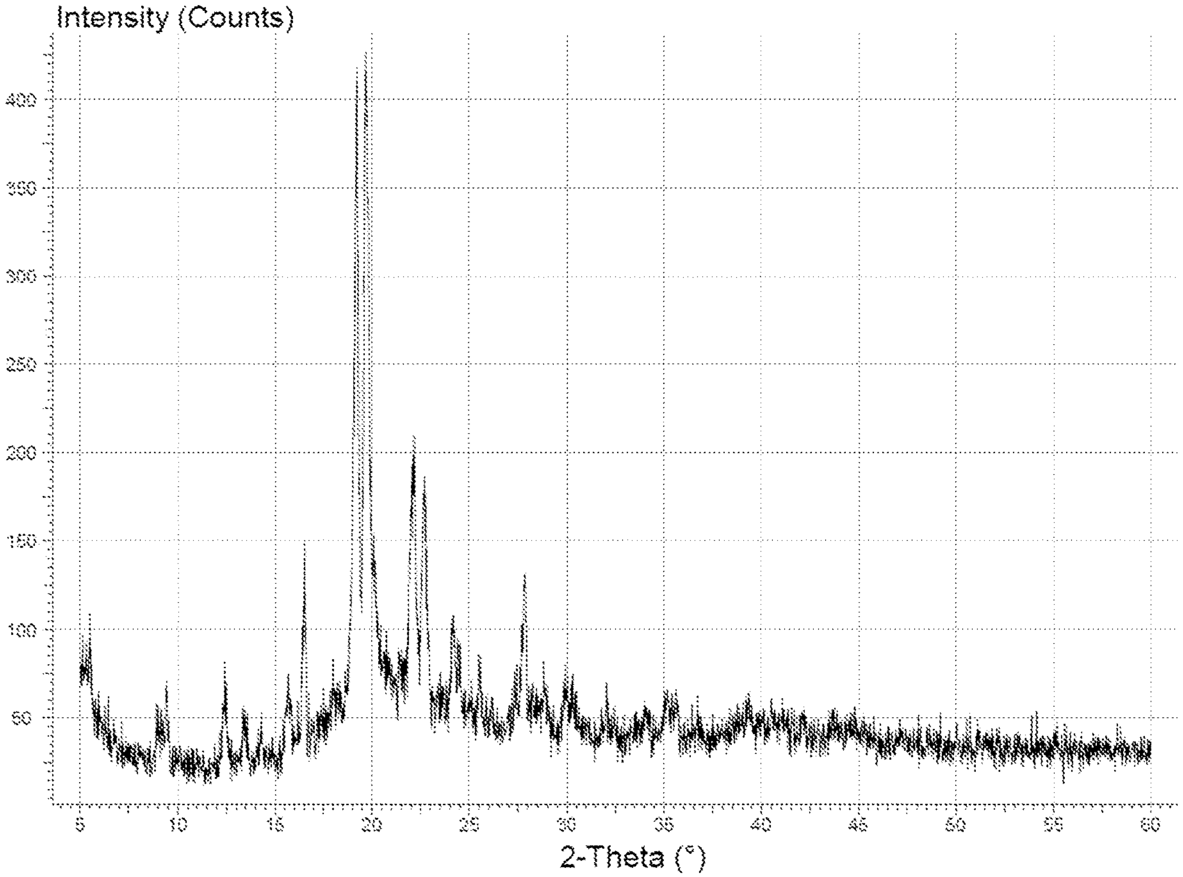

FIG. 7: XRPD pattern of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl) amino]benzoate (form C)

Figure 8:
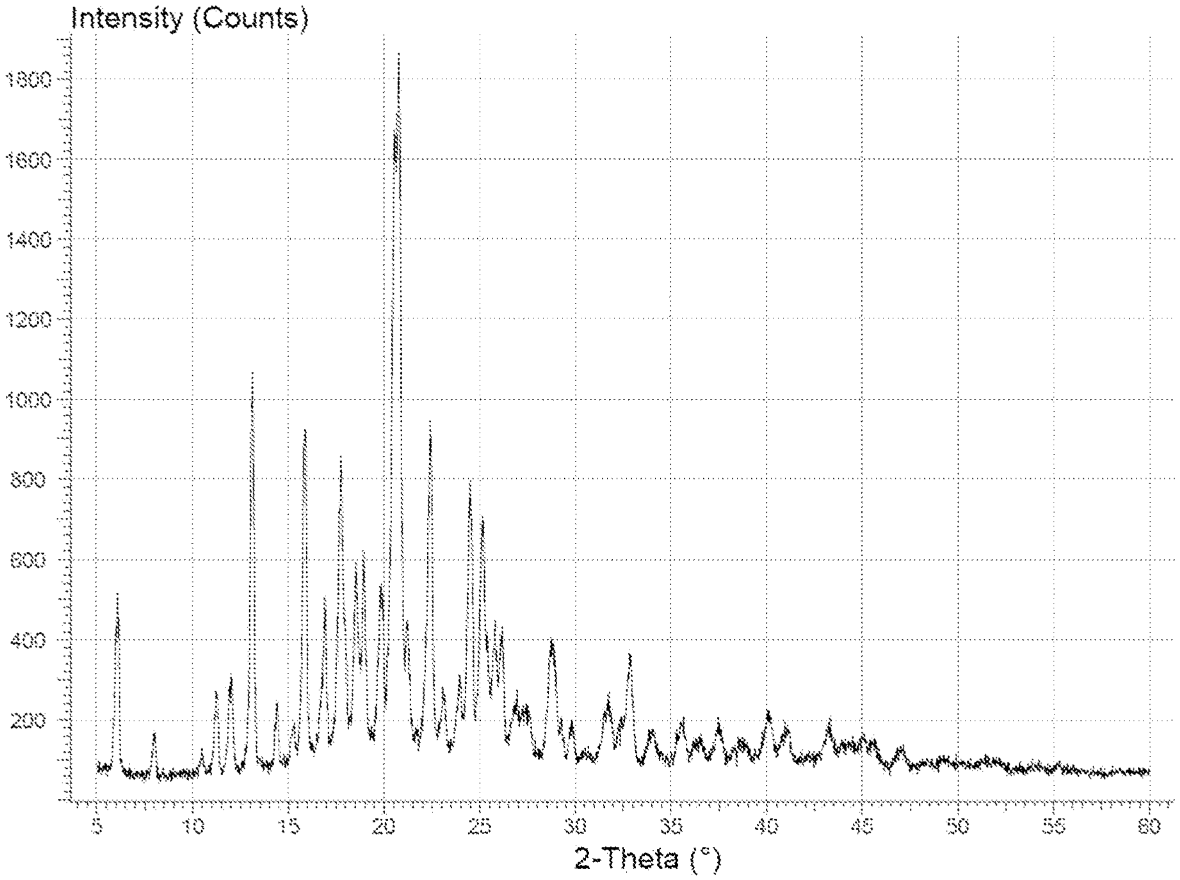

FIG. 8: XRPD pattern of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl) amino]benzoate (form D)

Figure 9:
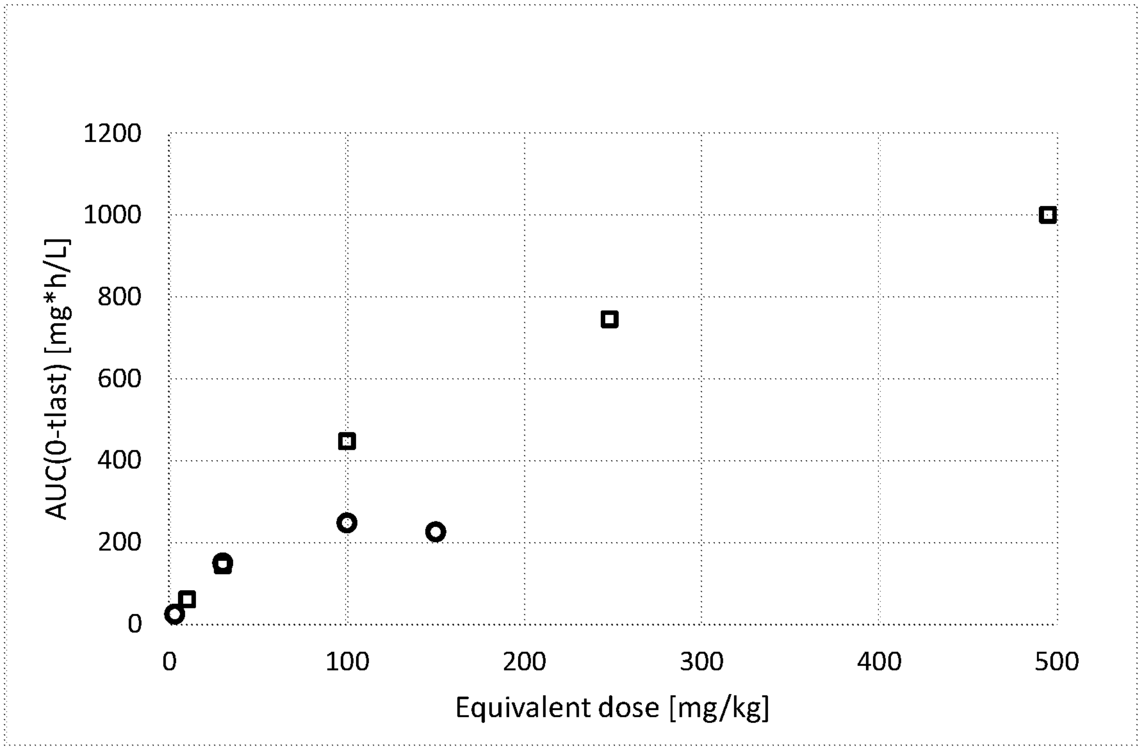
Figure 10:
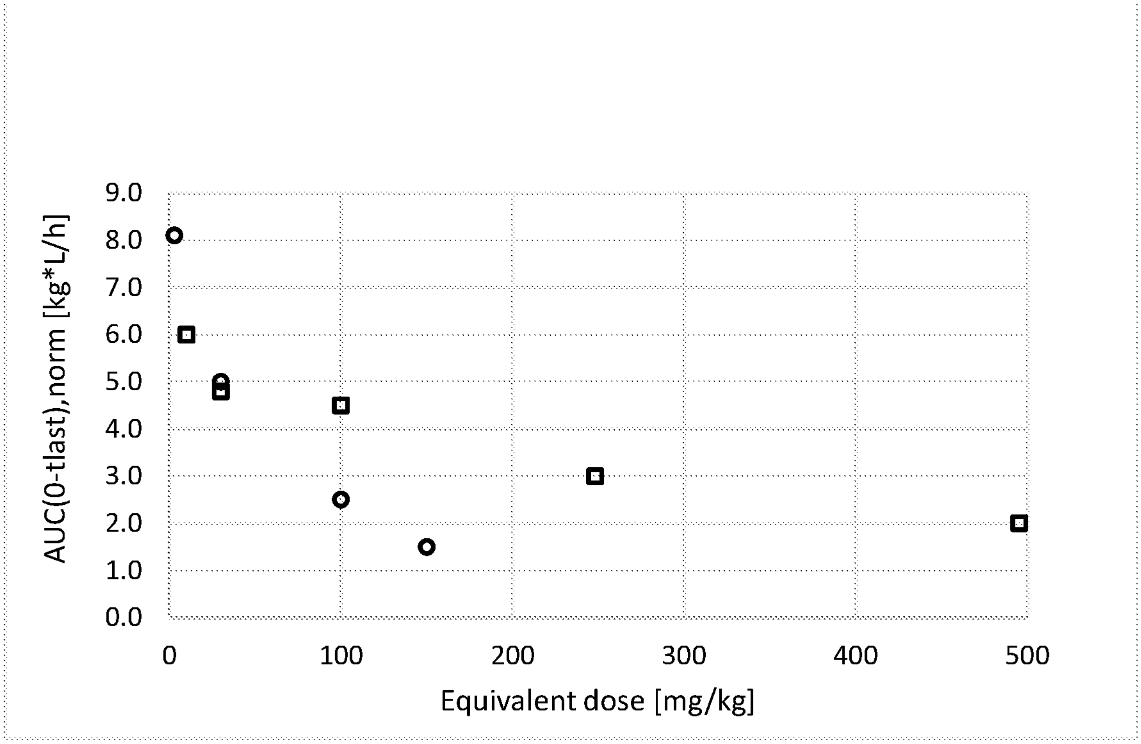
Figure 11A:
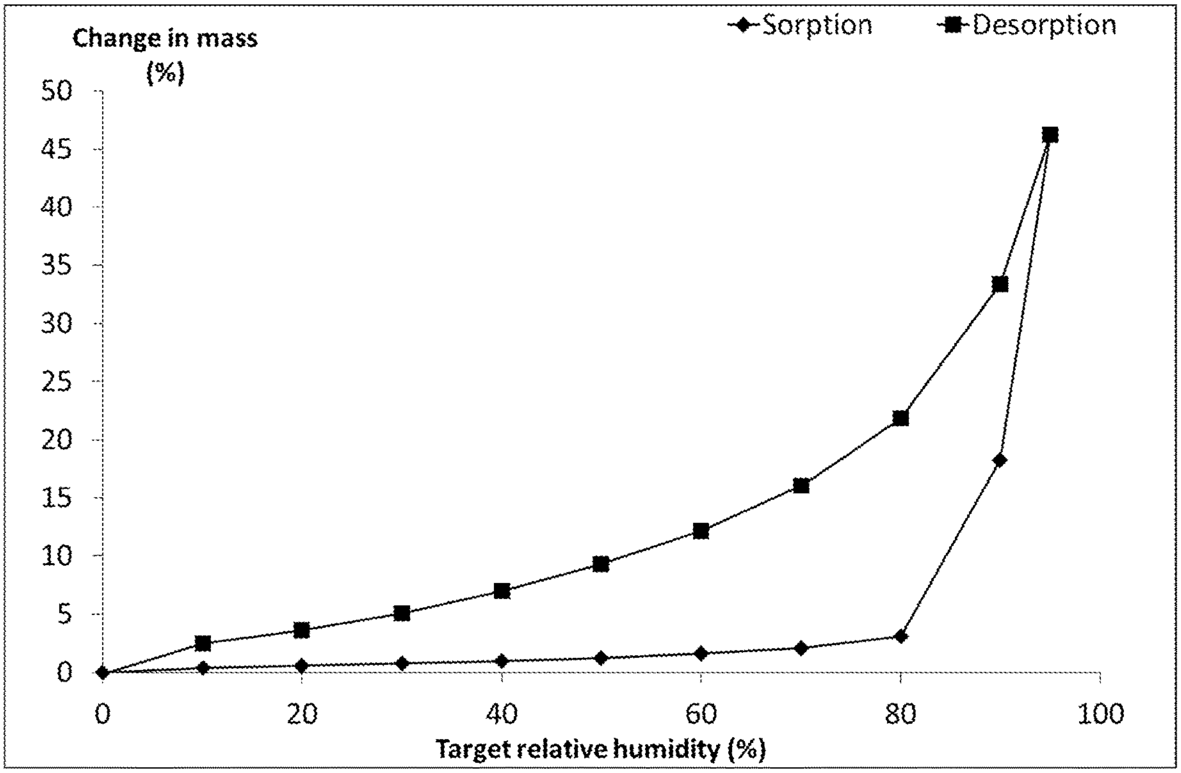
Figure 11B:
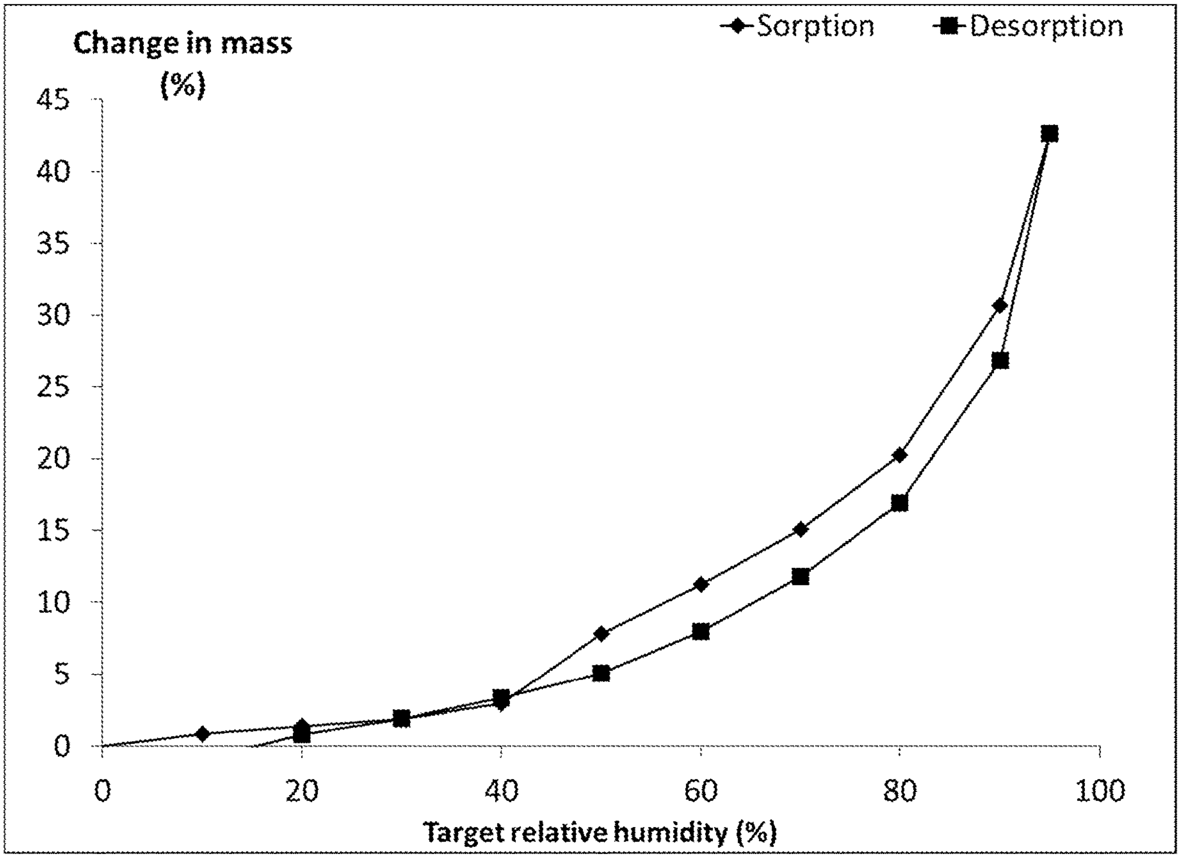
Figure 11C:
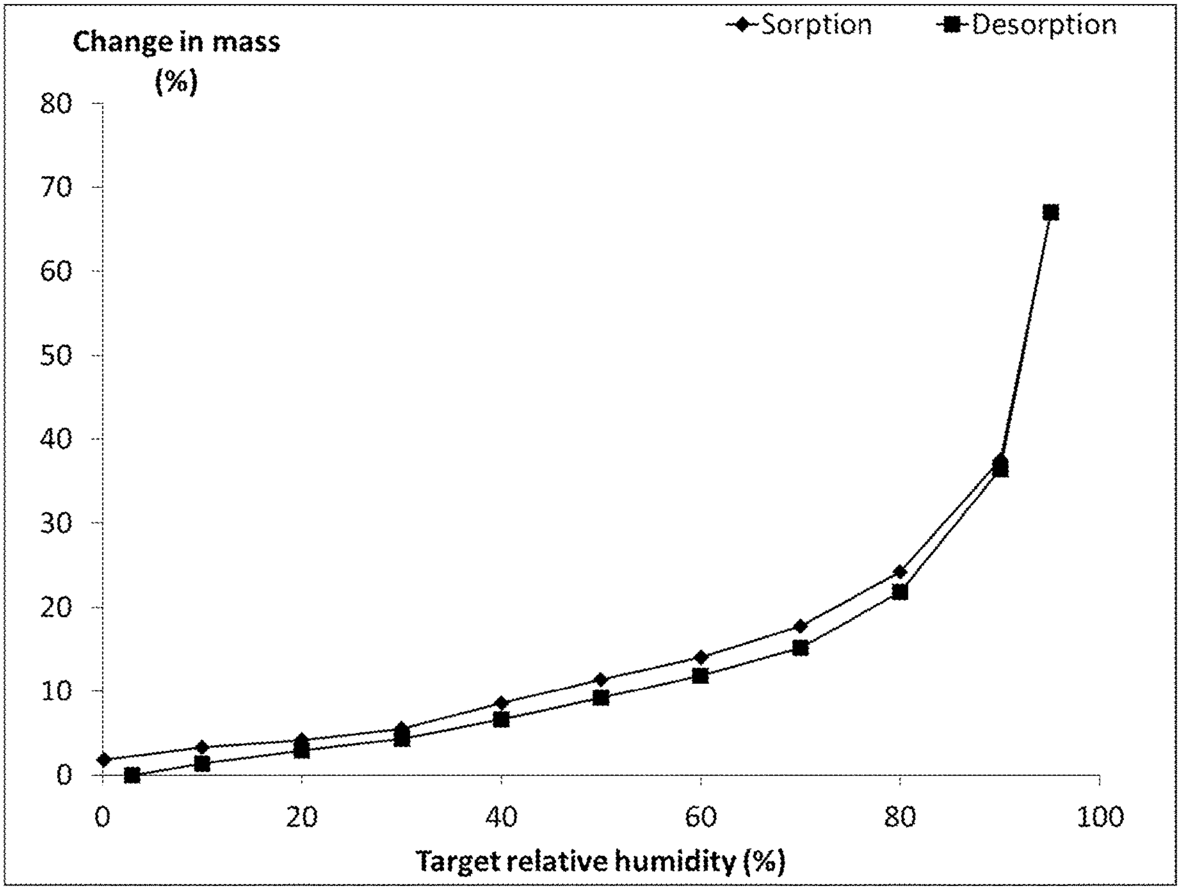
Figure 11D:
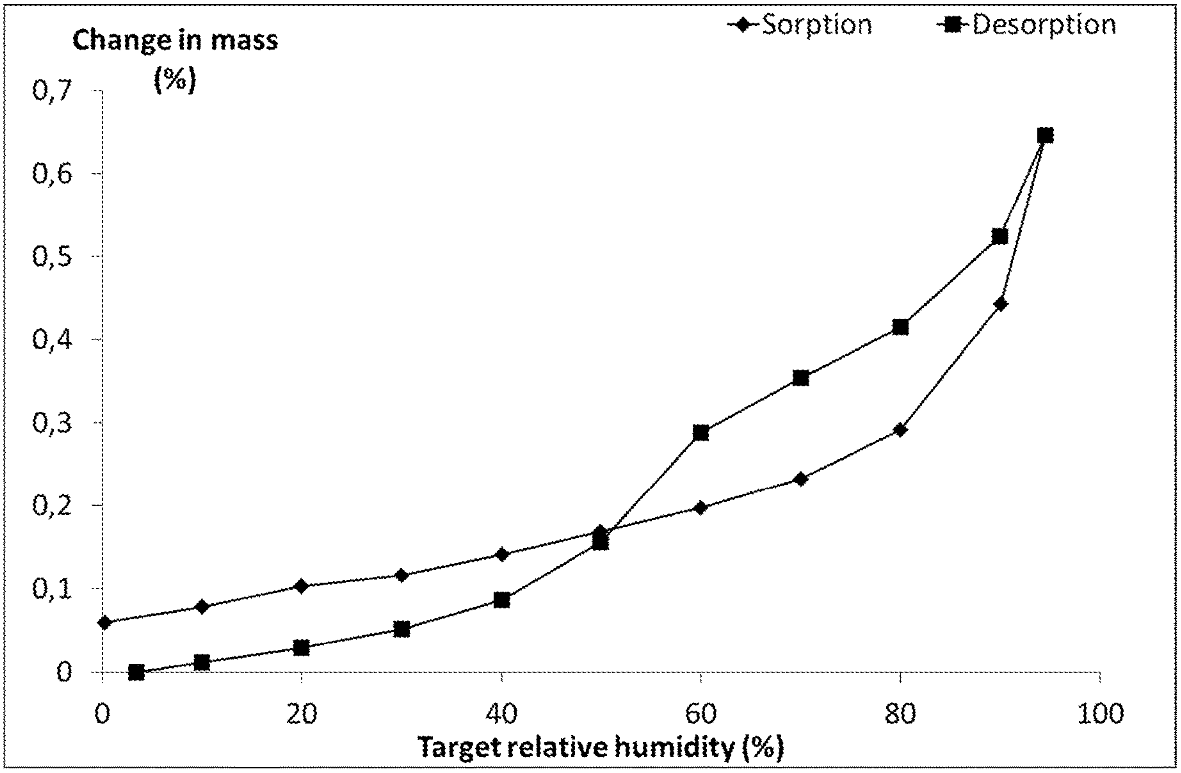
Figure 11E:
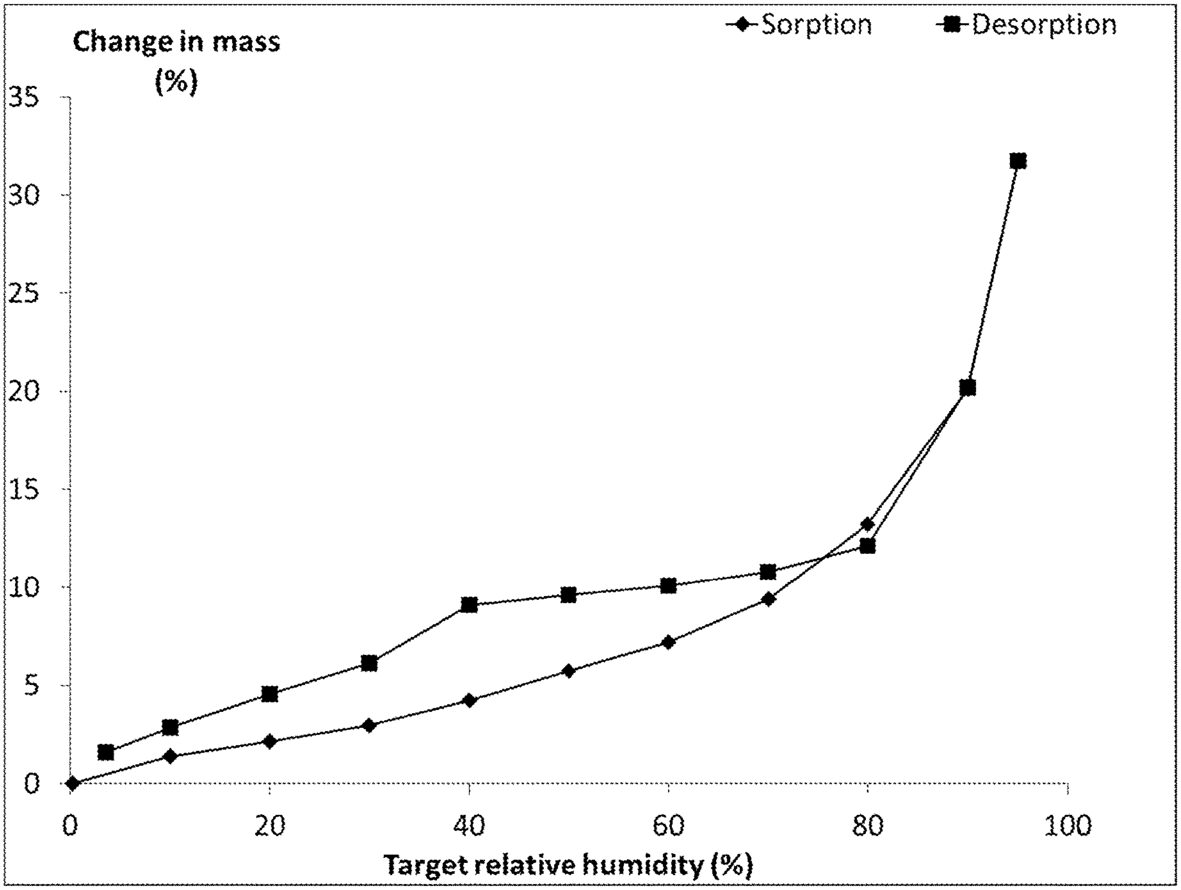
Figure 12A:
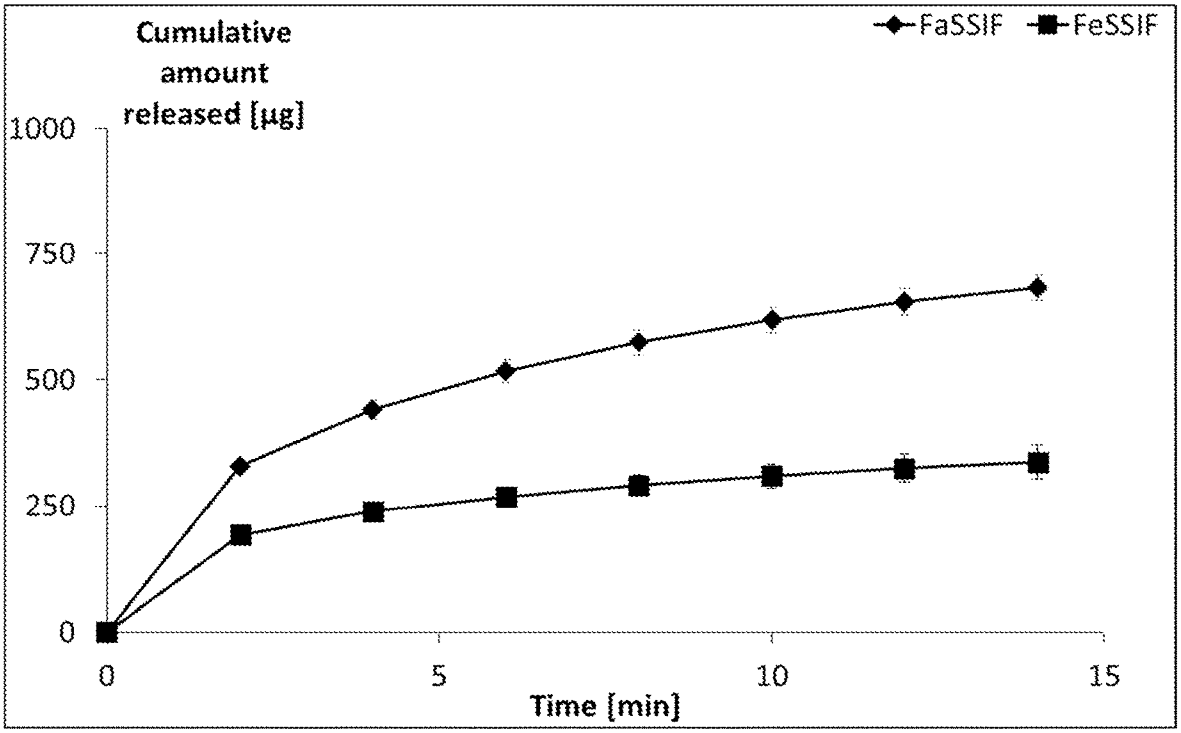
Figure 12B:
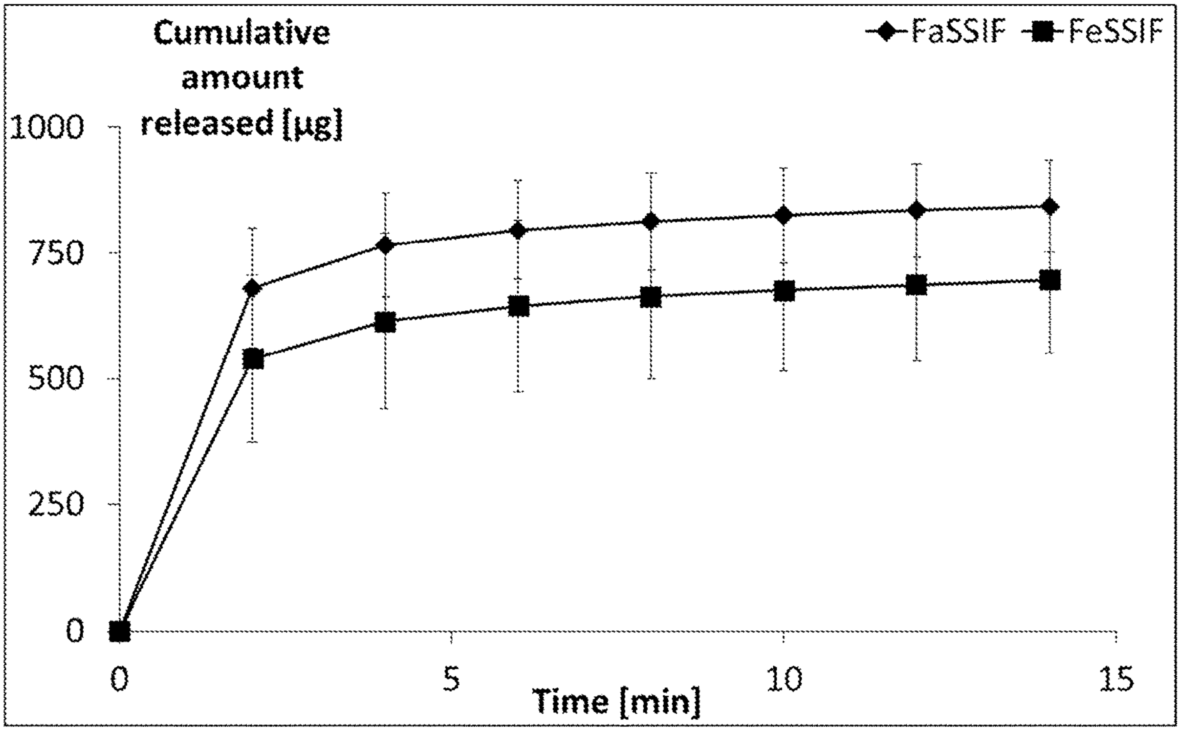
Figure 12C:
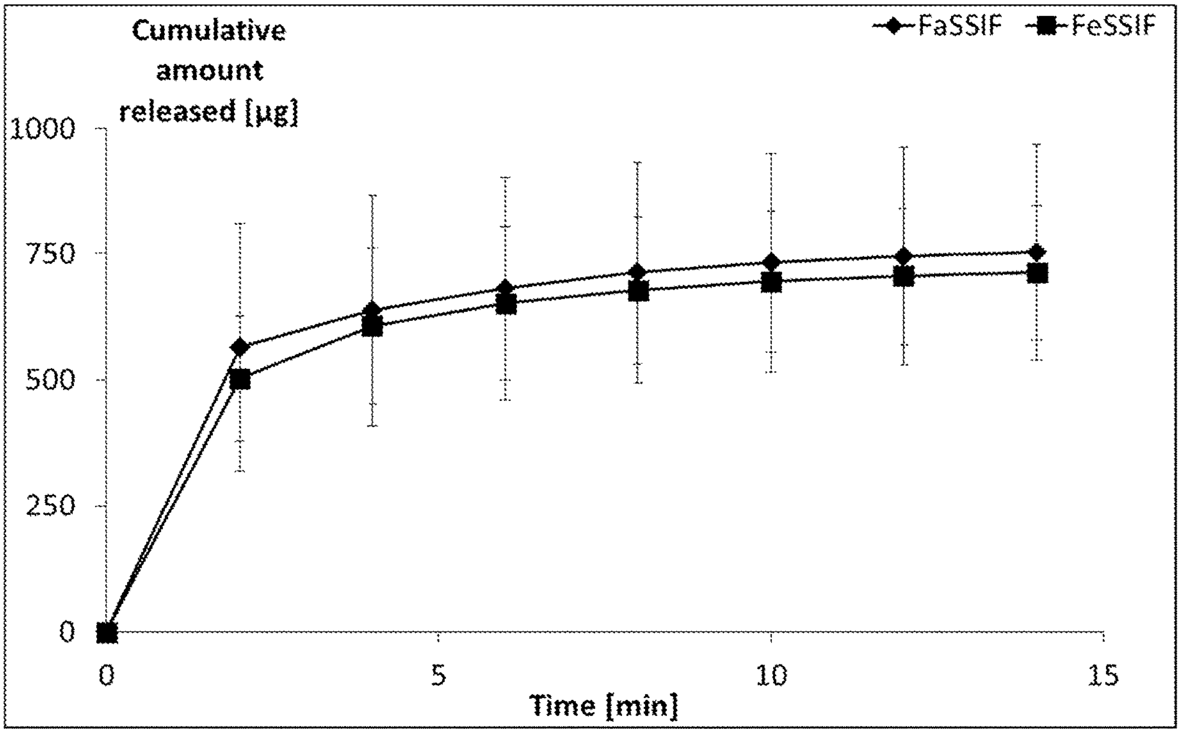
Figure 12D:
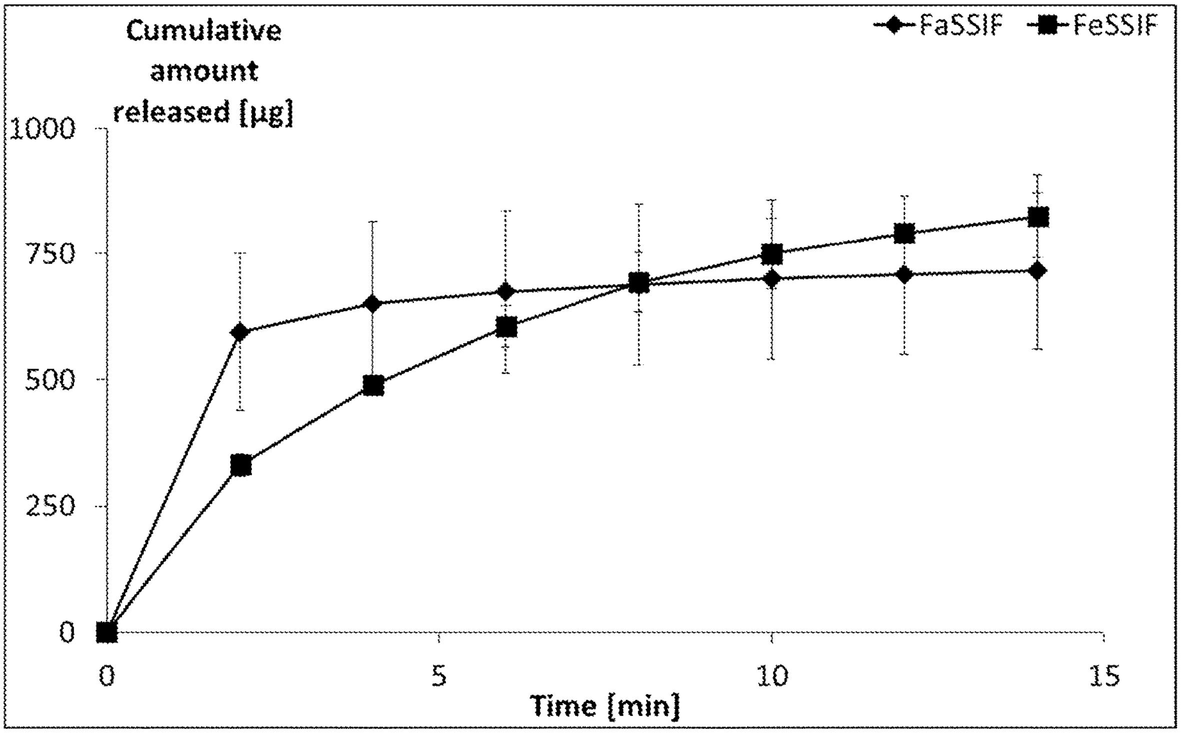
Figure 12E:
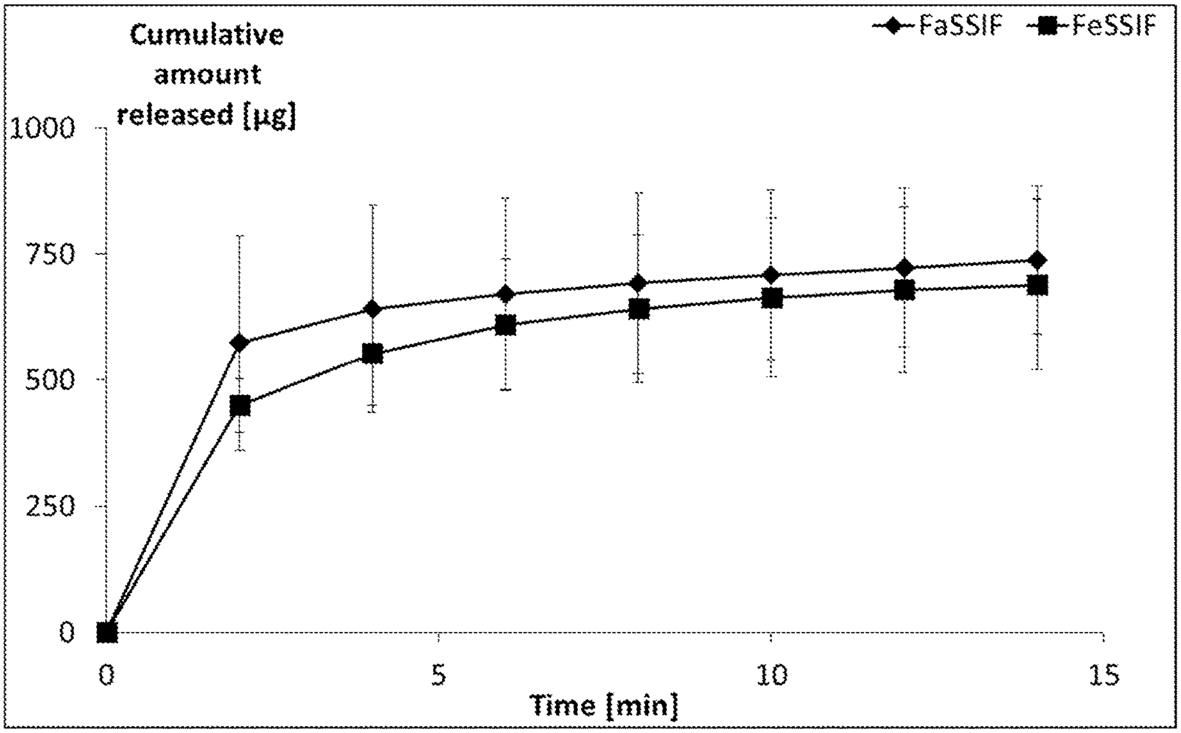

FIG. 9: Exposure (AUC) in rats of the free acid (circles) and cholinate salt (rectangles) after intragastric administration of different doses to rats FIG. 10: Plasma Exposure (AUC, dose-normalized to kg*L/h) in rats of the free acid after intragastric administration of different doses of either the free acid (circles) or the cholinate salt (rectangles) to rats FIG. 11: Isotherm plots of the DVS measurements FIG. 11*a*: Cholinate FIG. 11*b*: Sodium Salt FIG. 11*c* Potassium Salt FIG. 11*d* Arginin Salt FIG. 11 *e* Free Acid FIG. 12: Dissolution curves measured in FeSSIF and FaSSIF solution FIG. 12*a*: Free acid FIG. 12*b*: Cholinate FIG. 12*c* Sodium Salt FIG. 12*d* Potassium Salt FIG. 12 *e* Arginin Salt FIG. 13: overlay of the dissolution curves of the free acid and different saltforms FIG. 13*a* in FeSSIF Solution FIG. 13*b* in FassiF Solution

EXAMPLES

General Methods

DSC/TG

DSC thermograms were recorded using Differential Scanning Calorimeters (model DSC7, Pyris-1 or Diamond) from Perkin-Elmer. The measurements were performed with a heating rate of 20 $Kmin^{-1}$ using non-gastight aluminium pans. Flow gas was nitrogen. There was no sample preparation.

TGA thermograms were recorded using thermobalances (model TGA7 and Pyris 1) from Perkin-Elmer. The measurements were performed with a heating rate of 10 $Kmin^{-1}$ using open platinum pans. Flow gas was nitrogen. There was no sample preparation.

XRPD

X-Ray diffraction patterns were recorded at room temperature using XRD-diffractometers X'Pert PRO (PANalytical) (radiation Cu K alpha 1, wavelength 1.5406 Å). There was no sample preparation. All X-Ray reflections are quoted as °2Θ (theta) values (peak maxima) with a resolution of ±0.2°.

Analytical LCMS Methods

Method 1: Instrument: Waters Acquity Platform ZQ4000; column: Waters BEHC 18, 50 mm×2.1 mm, 1.7 μm; eluent A: water/0.05% formic acid, eluent B: acetonitrile/0.05% formic acid; gradient: 0.0 min 98% A→0.2 min: 98% A→1.7 min: 10% A→1.9 min: 10% A→2 min: 98% A→2.5 min: 98% A; flow: 1.3 ml/min; column temperature: 60° C.; UV-detection: 200-400 nm.

Method 2: Instrument: Agilent 1200 HPLC-system; column: Nucleodur C18 HTEC Silica/C18, 50 mm×2 mm, 2.0 μm; eluent A: phosphate buffer pH 2.4, eluent B: acetonitrile; gradient: 0.0 min 95% A→3 min: 60% A→3.5 min: 55% A→4.0 min: 50% A→4.5 min: 45% A→5.0 min: 20% A→6.0 min: 20% A→6.01 min: 95% A→7.0 min: 95% A; flow: 1.0 ml/min; column temperature: 40° C.; UV-detection: 220 nm. Solubility measurements were performed with method 2. All other measurements were performed with method 1.

Alternative Suzuki Cross-Coupling to Generate methyl-5-amino-2-(1-cyclobutyl-1H-pyrazol-4-yl) benzoate Scheme

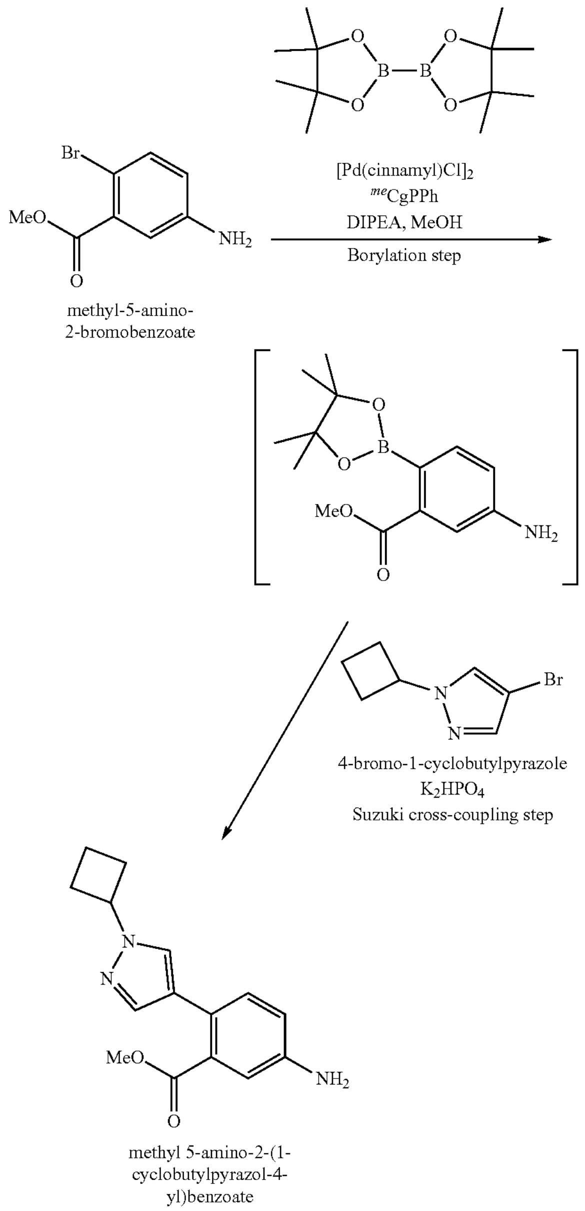

methyl-5-amino-2-bromobenzoate 4-bromo-1-cyclobutylpyrazole methyl 5-amino-2-(1-cyclobutylpyrazol-4-yl)benzoate Reaction vessel A was charged methyl-5-amino-2-bromobenzoate (1.00 wt, 1.0 eq; CAS-No: 6942-37-6) followed by methanol (8.0 vol) at a temperature of 15° C. to 25° C. The resulting solution was purged with nitrogen. Reaction vessel B was charged with bis(pinacolato)diboron (1.4 wt 1.3 eq; CAS No: 73183-34-3), and [Pd(cinnamyl)Cl]2 dimer (0.02 wt; CAS 12131-44-1) and meCgPPh (0.05 wt, 0.04 eq). Reaction vessel B was also purged with nitrogen. Then, the solution from reaction vessel A was mixed to reaction vessel B followed by addition of methanol (2.0 vol, 1.6 wt) as line/vessel rinse. N,N-diisopropylethylamine was added (2.3 vol, 3.0 eq), pre-purged with nitrogen, maintaining a temperature of 15° C. to 45° C. The solution was heated to a temperature of 40° C. to 45° C. and stirred for 2 to 4 h until the reaction was completed as confirmed by 1H NMR analysis.

Then, the solution was heated and maintained for 10 min at a temperature 55° C. to 65° C. and charged with a pre-nitrogen-sparged solution of 4-bromo-1-cyclobutylpyrazole (1.14 wt, 1.3 eq; CAS No: 1002309-50-3) dissolved in methanol (2.0 vol). Then, the solutions is mixed with a pre nitrogen sparged 5.2M $K_2HPO_4$ (aq) solution (5.0 vol, 6.0 eq.) for 30 min maintaining 55 to 65° C.

The reaction mixture was heated to 70° C. to 75° C. and stirred for 16 to 20 h. Thereafter, the reaction mixture was cooled to 15° C. to 25° C. and charged with purified water (3.7 vol) maintaining the temperature of 15° C. to 25° C. The two phases were separated and the organic phase was clarified by use of a 1 μm filter and rinsing the vessel/filter with methanol (1.0 vol).

The cleared organic layer was concentrated to 12.0 vol by evaporation at a temperature of 50° C. to 60° C. Isopropyl acetate (12.0 vol) was added and mixture was then concentrated to 12 vol at 50 to 60° C. This was repeated 4 consecutive times or until the residual methanol was ≤3.0% w/w as compared to (methyl 5-amino-2-(1-cyclobutylpyrazol-4-yl)benzoate) by $^1$H NMR analysis.

The reaction mixture was cooled to 15° C. to 25° C. and charged with purified water (10.0 vol) and isopropyl acetate (10.0 vol) while maintaining the temperature of 15° C. to 25° C. The mixture in the reaction vessel was stirred for 10 to 20 min. Thereafter, the two phases were separated. The organic layer was heated to 40° C. to 45° C. and charged with SiliaMetS (0.2 wt; Silicycle; R1030B). The reaction mixture was stirred at 40° C. to 45° C. for at least 1 hour. Then the reaction mixture was filtered to remove the silica, followed by two consecutive washing steps with isopropyl acetate (2.0 vol) at 40° C. to 45° C. The filtrates were combined and then heated to 50° C. to 60° C. and concentrated by evaporation to 3.0 vol.

n-heptane (6.0 vol) was added to the concentrated clarified filtrates while maintaining 50° C. to 60° C. over at least 30 minutes. Thereafter, the mixture was cooled to 0° C. to 5° C. over at least 90 minutes and then stirred for 4 h. over the mixture was then filtered with a 20 μm cloth at 0° C. to 5° C. and filter cake was washed with pre-mixed isopropyl acetate (0.66 vol) and n-heptane (1.34 vol) at 0° C. to 5° C. The filter cake was slurry washed with purified water (2.0 vol) for at least 20 minutes at 15° C. to 25° C., followed by slurry washing of the filter cake with n-heptane (2.0 vol) for at least 20 minutes at 15° C. to 25° C. The filter cake was then washed again with n-heptane, (2.0 vol, 1.4 wt). The material was tried under vacuum and a flow of nitrogen for at least 6 h at 50° C. or until water content was 1.5% w/w, isopropyl acetate was 1.0% w/w and was n-heptane≤1.0% w/w as compared to the product (Methyl 5-amino-2-(1-cyclobutylpyrazol-4-yl)benzoate). Methyl 5-amino-2-(1-cyclobutylpyrazol-4-yl)benzoate was obtained as a solid in a yield of 50% to 70%.

$^1$H NMR (400 MHz, DMSO-d6) δ 7.73 (d, J=0.7 Hz, 1H), 7.37 (d, J=0.7 Hz, 1H), 7.11 (d, J=8.5 Hz, 1H), 6.80 (d, J=2.5 Hz, 1H), 6.70 (dd, J=8.4 Hz, 1H), 5.32 (bs, 2H), 4.79 (quint, 1H), 3.69 (s, 3H), 2-48-2.42 (m, 1H), 2.41-2.32 (m, 2H), 1.81-1.72 (m, 2H).

Example 1

The cholinate according to the invention was obtained in form A by two alternative approaches, which are described as Example 1 a) and b):

a) 2-Hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate Form A

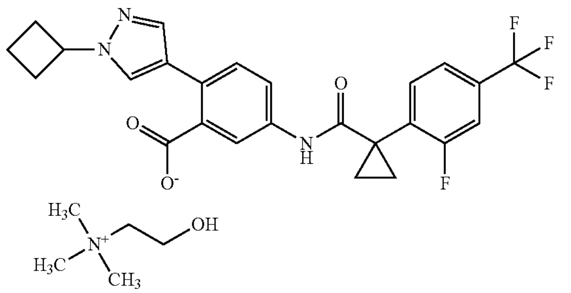

2-(1-Cyclobutyl-1H-pyrazol-4-yl)-5-[({1-[2-fluoro-4-(trifluoromethyl)phenyl]cyclopropyl}carbonyl)amino]benzoic acid was prepared as disclosed in WO 2018/114786 A1, Example 3.

2-(1-Cyclobutyl-1H-pyrazol-4-yl)-5-[({1-[2-fluoro-4-(trifluoromethyl)phenyl]cyclopropyl}carbonyl)amino]benzoic acid (10.0 g, 20.5 mmol) was suspended in 98 mL iso-butanol, then choline hydroxide solution (CAS 123-41-1, 46 wt % in water, 5.45 g, 20.5 mmol) was added and the mixture turned clear after stirring for 10 min at 22° C. The clear solution was stirred for 18 h at 22° C., after which time the solvent was evaporated via co-distillation with 2×50 mL toluene. The obtained solid was dissolved in 170 mL refluxing acetonitrile over 3 hours. The solution was cooled with gentle stirring and precipitation was observed at 48° C. The mixture was then cooled to 5° C., stirred for 1 hour. The formed crystallisate was isolated by filtration, washed with 2×10 mL acetonitrile at the same temperature and dried overnight in the drying cabinet (40° C., 200 mBar) to yield 11.2 g (yield 91.9%) of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carb onyl)amino]benzoate as a colourless crystalline solid, crystallized as form A.

$^1$H NMR (600 MHz, DMSO-d6) δ[ppm]1.15-1.17 (m, 2H), 1.59-1.60 (m, 2H), 1.72-1.80 (m, 2H), 2.33-2.40 (m, 2H), 2.41-2.52 (m, 2H), 3.09 (s, 9H), 3.38-3.39 (m, 2H), 3.82 (s, br, 2H), 4.75 (quint, 1H), 5.66 (s, br, 1H), 7.09 (d, 1H), 7.20 (d, 1H), 7.30 (dd, 1H), 7.58 (d, 1H), 7.65-7.70 (m, 2H), 7.72 (s, 1H), 8.04 (s, 1H), 8.78 (s, 1H).

b) 2-Hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate Form A 2-(1-Cyclobutyl-1H-pyrazol-4-yl)-5-[({1-[2-fluoro-4-(trifluoromethyl)phenyl]cyclopropyl}carbonyl)amino]benzoic acid was prepared as disclosed in WO 2018/114786 A1, Example 3.

As an alternative to Example 1b) a further process of salt formation was used. Therefore, 487 mg of 2-(1-cyclobutyl-1H-pyrazol-4-yl)-5-[({1-[2-fluoro-4-(trifluoromethyl)phenyl]cyclopropyl}carbonyl)amino]benzoic acid was dissolved in 200 mL acetonitrile at 70° C. After clarification, 242 mg of an aqueous choline hydroxide solution (CAS 123-41-1, ca. 50%) was added and the clear solution was stirred for one hour at room temperature. The solvent was then slowly evaporated at room temperature until a dry solid was obtained. The solid corresponded to 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate form A.

Example 2: Crystallisation of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate mono 2-propanol solvate (Form B)

25.27 mg of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate as obtained in accordance with Example 1 was suspended in 40 volumes of 2-propanol at room temperature. Upon heating to 80° C., the solid was completely dissolved (clear point) at 50° C. Upon cooling down to −15° C., crystallization was observed at 25° C. The suspension was then filtered and 17.74 mg of solid was obtained. The XRPD pattern corresponds to the 2-propanol solvate. This solvate is also named as “form B”

Example 3: 2-Hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate Form C 150 mg of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate as obtained in accordance with Example 1 were dissolved in 5 mL of 2-propanol/water mixture (9:1 vol:vol). The solution was clarified by filtration through a 2 µm PTFE syringe filter, then left standing at 20° C. in a scintillation vial sealed with a cap of aluminium pierced twice, until the solvent was completely evaporated. The resulting solid corresponds to form C.

Example 4: 2-Hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate 125.48 mg of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate as obtained in accordance with Example 1 was dissolved in 0.5 mL of hexafluoropropan-2-ol in a small vessel. The smaller vessel was placed open in a larger vessel containing diethyl ether. The vessel set-up was allowed to stand undisturbed at room temperature to allow solvent diffusion across into the smaller vessel and promote the crystallization of 125.48 mg of 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate. After several days, 92.18 mg of solid was isolated by filtration, and dried at 40° C. under reduced pressure for approximately 20 h. The solid was also named as form D. However, it turned out that it is a hexafluoropropan-2-ol solvate.

Example 5: Amorphous Sodium 2-(1-cyclobutyl-1H-pyrazol-4-yl)-5-[({1-[2-fluoro-4-(trifluoromethyl) phenyl]cyclopropyl}carbonyl)amino]benzoate 487 mg of 2-(1-cyclobutyl-1H-pyrazol-4-yl)-5-[({1-[2-fluoro-4-(trifluoromethyl)phenyl]cyclopropyl}carbonyl) amino]benzoic acid was dissolved in 300 mL of acetonitrile at 70° C. Then, 1 mL of a aqueous molar solution of sodium hydroxide was added. The solvent was then evaporated at room temperature resulting in a solid. The solid corresponds to an amorphous sodium 2-(1-cyclobutyl-1H-pyrazol-4-yl)-5-[({1-[2-fluoro-4-(trifluoromethyl) phenyl] cyclopropyl}carbonyl)amino]benzoate.

Example 6: Partially Crystalline Sodium 2-(1-cyclobutyl-1H-pyrazol-4-yl)-5-[({1-[2-fluoro-4-(trifluoromethyl) phenyl]cyclopropyl}carbonyl)amino] benzoate

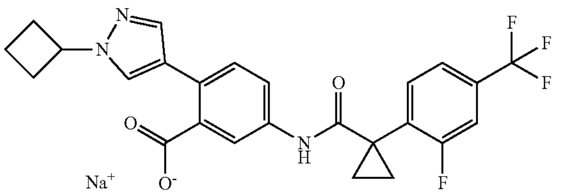 [SMILES: O=C([O-])c1cc(NC(=O)C2(c3ccc(C(F)(F)F)cc3F)CC2)ccc1-c1cnn(C2CCC2)c1 ; [Na+]]

2-(1-Cyclobutyl-1H-pyrazol-4-yl)-5-[({1-[2-fluoro-4-(trifluoromethyl)phenyl]cyclopropyl}carbonyl)amino]benzoic acid (540 mg, 1.12 mmol) and sodium hydroxide (44.3 mg, 1.12 mmol) were stirred in 11 mL water at 80° C. until a clear solution formed. The mixture was evaporated to dryness. Residual water was removed by repeated azeotropic distillation with toluene (20 mL). The obtained solid was amorphous as proven by XRPD measurement (data not shown). The solid was dissolved in acetone (5 mL) and stored in the freezer (−18° C.) for 6 weeks. The formed amorphous solid was filtered off and dried in the drying cabinet (40° C.) to yield 140 mg (yield 25%) of the sodium 2-(1-cyclobutyl-1H-pyrazol-4-yl)-5-[({1-[2-fluoro-4-(trifluoromethyl) phenyl]cyclopropyl}carbonyl)amino]benzoate as a solid. It turned out to be only partially crystalline; see FIG. 5.

$^1$H NMR (400 MHz, DMSO-d6) δ[ppm]1.15-1.18 (m, 2H), 1.58-1.60 (m, 2H), 1.72-1.81 (m, 2H), 2.32-2.48 (m, 4H), 4.75 (quint, 1H), 7.11 (d, 1H), 7.20 (d, 1H), 7.29 (dd, 1H), 7.56-7.58 (m, 1H), 7.64-7.70 (m, 2H), 7.72 (s, 1H), 8.04 (s, 1H), 8.78 (s, 1H).

LCMS: Rt=1.24 min; MS (ESIPos) m/z=488 (M+H acid)$^+$.

Example 7: Crystalline Sodium 2-(1-cyclobutyl-1H-pyrazol-4-yl)-5-[({1-[2-fluoro-4-(trifluoromethyl) phenyl]cyclopropyl}carbonyl)amino]benzoate 0.1165 g of the solid obtained in example 6 was suspended in 0.669 g of acetone, resulting in a thin suspension. The solvent was then slowly evaporated over more than a week at room temperature until a solid was obtained. The crystallinity of the sample was assessed by XPRD; see Example 10.

Example 8: Amorphous Potassium 2-(1-cyclobutyl-1H-pyrazol-4-yl)-5-[({1-[2-fluoro-4-(trifluoromethyl) phenyl]cyclopropyl}carbonyl)amino]benzoate 487 mg of 2-(1-cyclobutyl-1H-pyrazol-4-yl)-5-[({1-[2-fluoro-4-(trifluoromethyl)phenyl]cyclopropyl} carbonyl) amino]benzoic acid that was prepared as disclosed in WO 2018/114786 A1, Example 3, was dissolved in 300 mL acetonitrile at 70° C. After clarification, 1 mL of a molar aqueous solution of potassium hydroxide was added. The solvent was then slowly evaporated at room temperature until a dry solid was obtained. The XPRD analysis of the obtained solid was characteristic of an amorphous substance.

Example 9: Amorphous Arginine salt of 2-(1-cyclobutyl-1H-pyrazol-4-yl)-5-[({1-[2-fluoro-4-(trifluoromethyl) phenyl]cyclopropyl}carbonyl)amino] benzoate 487 mg of 2-(1-cyclobutyl-1H-pyrazol-4-yl)-5-[({1-[2-fluoro-4-(trifluoromethyl)phenyl]cyclopropyl} carbonyl) amino]benzoic acid that was prepared as disclosed in WO 2018/114786 A1, Example 3, was dissolved in 200 mL acetonitrile at 70° C. After clarification, 174 mg of arginine was added. The solvent was then slowly evaporated at room temperature until a dry solid was obtained. The XPRD analysis of the obtained solid was characteristic of an amorphous substance.

Example 10: XRPD Characterization of Polymorphic and Pseudopolymorphic Forms of Salts of 2-(1-cyclobutyl-1H-pyrazol-4-yl)-5-[({1-[2-fluoro-4-(trifluoromethyl)-phenyl]cyclopropyl}carbonyl) amino]benzoic acid X-Ray diffraction patterns of polymorphic form A of the cholinate salt and obtained solids of Examples 5 to 7, i.e. the sodium salt were recorded at room temperature using XRPD-diffractometers X'Pert PRO (PANalytical) (radiation Cu K alpha 1, wavelength 1.5406 Å). There was further no sample preparation. All X-Ray reflections are quoted as °2Θ (theta) values (peak maxima) with a resolution of ±0.2°.

X-Ray powder diffraction (XRPD) analyses of form B, form C and form D of the cholinate were carried out using a Bruker D2 Phaser powder diffractometer equipped with a LynxEye detector. The specimens underwent minimum preparation but, if necessary they were lightly milled in a pestle and mortar before acquisition. The specimens were located at the centre of a silicon sample holder within a 5 mm pocket (ca. 5 to 10 mg).

TABLE 1

Lits of peak maxima for the tested polymorphic/pseudopolymorphic forms of the cholinate according to the invention and the sodium salt
Reflections (Peak maxima) [2 Theta]

| Polymorphic form A of the cholinate (Example 1b)) | Mono 2-propanol solvate of the cholinate (Example 2) | Polymorphic form C of the cholinate (Example 3) | Polymorphic form D of the cholinate (Example 4) | crystalline form of the sodium salt (Example 7) |
|---|---|---|---|---|
| 12.99 | 18.15 | 9.45 | 20.60 | 5.12 |
| 20.42 | 5.48 | 12.42 | 20.72 | 10.97 |

TABLE 1-continued

Lits of peak maxima for the tested polymorphic/pseudopolymorphic forms of the cholinate according to the invention and the sodium salt
Reflections (Peak maxima) [2 Theta]

| Polymorphic form A of the cholinate (Example 1b)) | Mono 2-propanol solvate of the cholinate (Example 2) | Polymorphic form C of the cholinate (Example 3) | Polymorphic form D of the cholinate (Example 4) | crystalline form of the sodium salt (Example 7) |
|---|---|---|---|---|
| 20.64 | 19.05 | 15.72 | 13.09 | 11.45 |
| 18.84 | 20.69 | 16.51 | 15.86 | 11.50 |
| 22.32 | 23.76 | 19.19 | 22.41 | 16.43 |
| 15.74 | 16.47 | 19.70 | 17.75 | 19.37 |
| 20.75 | 11.19 | 20.06 | 24.49 | 12.74 |
| 24.42 | 19.62 | 22.10 | 25.13 | 17.22 |
| 17.62 | 22.88 | 22.67 | 18.94 | 13.75 |
| 18.41 | 19.47 | 24.15 | 18.55 | 22.63 |

Example 11: IR Data for Form a of the Cholinate According to the Invention

IR

IR-ATR-spectrum of form A of the cholinate according to the invention and as prepared as outlined in Example 1 were recorded at room temperature using a FT-IR-spectrophotometer using a Tensor 37 device from Bruker. Resolution was 2 $cm^{-1}$.

TABLE 2

Lits of band maxima for form A of the cholinate accordingto the invention
Band maxima ($cm^{-1}$)

| | |
|---|---|
| 560.3 | 1256.5 |
| 610.4 | 1308.6 |
| 636.5 | 1324 |
| 666.3 | 1340.4 |
| 672.1 | 1351 |
| 678.9 | 1358.7 |
| 694.3 | 1375.1 |
| 731 | 1407.9 |
| 745.4 | 1422.4 |
| 756 | 1433.9 |
| 788.8 | 1448.4 |
| 807.1 | 1480.2 |
| 817.7 | 1530.4 |
| 835.1 | 1561.2 |
| 843.8 | 1572.8 |
| 873.7 | 1599.8 |
| 890.1 | 1653.8 |
| 910.3 | 2341.4 |
| 953.7 | 2360.6 |
| 959.5 | 2857.3 |
| 965.3 | 2875.6 |
| 978.8 | 2911.3 |
| 1013.5 | 2943.1 |
| 1035.7 | 2977.8 |
| 1056.9 | 3008.7 |
| 1082.9 | 3031.8 |
| 1090.6 | 3037.6 |
| 1122.5 | 3076.2 |
| 1164.9 | 3109.9 |
| 1183.2 | 3157.2 |
| 1215 | 3258.4 |
| 1235.3 | |

Example 12: Solubility Free Acid Vs. Salt

The solubility of the crystalline 2-(1-cyclobutyl-1H-pyrazol-4-yl)-5-[({1-[2-fluoro-4-(trifluoromethyl)phenyl]cyclopropyl}carbonyl)amino]benzoic acid (free acid) prepared as described in Example 3 of WO 2018/114786 A1, as well as cholinate form A was determined according to the shake-flask method (1 mL scale, stirred overnight) at 25° C.

TABLE 3

Solubility of free acid and cholinate according to the invention

| Solvent | Solubility of cholinate [mg/L] | Solubility of free acid [mg/L] |
|---|---|---|
| Water | >12500** | <1* |
| Phosphate buffer pH 8 | 10798 | 970 |
| Phosphate buffer pH 7 | 1019 | 87 |
| Acetate buffer pH 4.5 | 2 | <1 |
| 0.1M HCl | <1 | <1 |
| Ethanol | >12500 | 4260 |
| Acetonitrile | 3797 | 1290 |
| Acetone | 412 | 10100 |
| PEG 400 | 19159 | 6830 |
| Solutol/Ethanol/Water (40/10/50 V/V/V) | >35000 | 1300 |

*pH of the clear solution: 4.6
**pH of the clear solution: 8.32, pH of water before stirring: 5.57

Example 13: Determination of Exposure in Rat after Intragastric Administration

Method

Determination of exposure after intragastric application of test compounds was performed in female conscious rats with a body weight of 0.2 kg (minimum) to 0.25 kg (maximum). The test compounds were applied as bolus via intragastric probe to unfed female rats in solution or suspension in the vehicle ethanol/solutol/water (v/v/v 10/40/50).

At the indicated timepoints between 8 min and 24 h after dosing, 150 µl blood were sampled via a catheter from the vena jugularis. The samples were treated with K-EDTA as anticoagulant and stored cooled until further processing (refrigerator, 4° C.). The samples were centrifuged (15 min, 3000 rpm), then an aliquot of 100 µL was taken from the supernatant (plasma), precipitated by addition of 400 µL cold acetonitrile or methanol (abs.) and frozen at −20° C. over night. The samples were centrifuged (15 min, 3000 rpm), then 150 µL of the clear supernatant were taken for analytical testing. Analytics were performed using an Agilent 1200 HPLC-system with LCMS/MS detection.

Calculation of PK parameters (via PK calculation software, e.g. WinNonLin®):

$AUC_{(0\text{-}tlast)}$: Area under the plasma concentration-time-profile from timepoint zero to last time point 24 h (in kg*L/h);

$AUC_{(0\text{-}tlast)\ norm}$: Integrated area under the plasma concentration-time-profile from timepoint zero to last time point 24 h, divided by the body weight normalized dose (in kg*L/h);

$C_{max}$: Maximal concentration of the test compound in plasma (in µg/L);

$C_{max,norm}$: Maximal concentration of the test compound in plasma, divided by the body weight normalized dose (in kg/L).

Results

The exposure in rat's plasma of 2-(1-cyclobutyl-1H-pyrazol-4-yl)-5-[({1-[2-fluoro-4-(trifluoromethyl)-phenyl]cyclopropyl}carbonyl)amino]benzoic acid (free acid) was determined after application of various doses of either the free acid itself or 2-hydroxy-N,N,N-trimethylethanaminium 2-(1-cyclobutyl-1H-pyrazol-4-yl)-5-[({1-[2-fluoro-4-(trifluoromethyl)phenyl]cyclopropyl}carbonyl)amino]benzoate (cholinate). The applied dose of cholinate according to the invention was adjusted as compared to free acid according to the difference in molecular weight. The resulting equivalent doses were used for comparison.

The achieved AUC or $AUC_{norm}$ respectively, were compared as a function of dose.

TABLE 4

Dose dependent exposure of the free acid in rat's plasma after application of the cholinate according to the invention vs. free acid according to the invention (free acid) in rat

| Dose equiv. | AUC(0-tlast) [mg · h/L] | | $AUC(0\text{-tlast})_{norm}$ [kg*L/h] | |
|---|---|---|---|---|
| [mg/kg] | free acid | cholinate | free acid | cholinate |
| 3 | 24 | | 8.1 | |
| 10 | | 60 | | 6.0 |
| 30 | 149 | 146 | 5.0 | 4.8 |
| 100 | 247 | 447 | 2.5 | 4.5 |
| 150 | 225 | | 1.5 | |
| 248 | | 745 | | 3.0 |
| 495 | | 1000 | | 2.0 |

Figure 4:
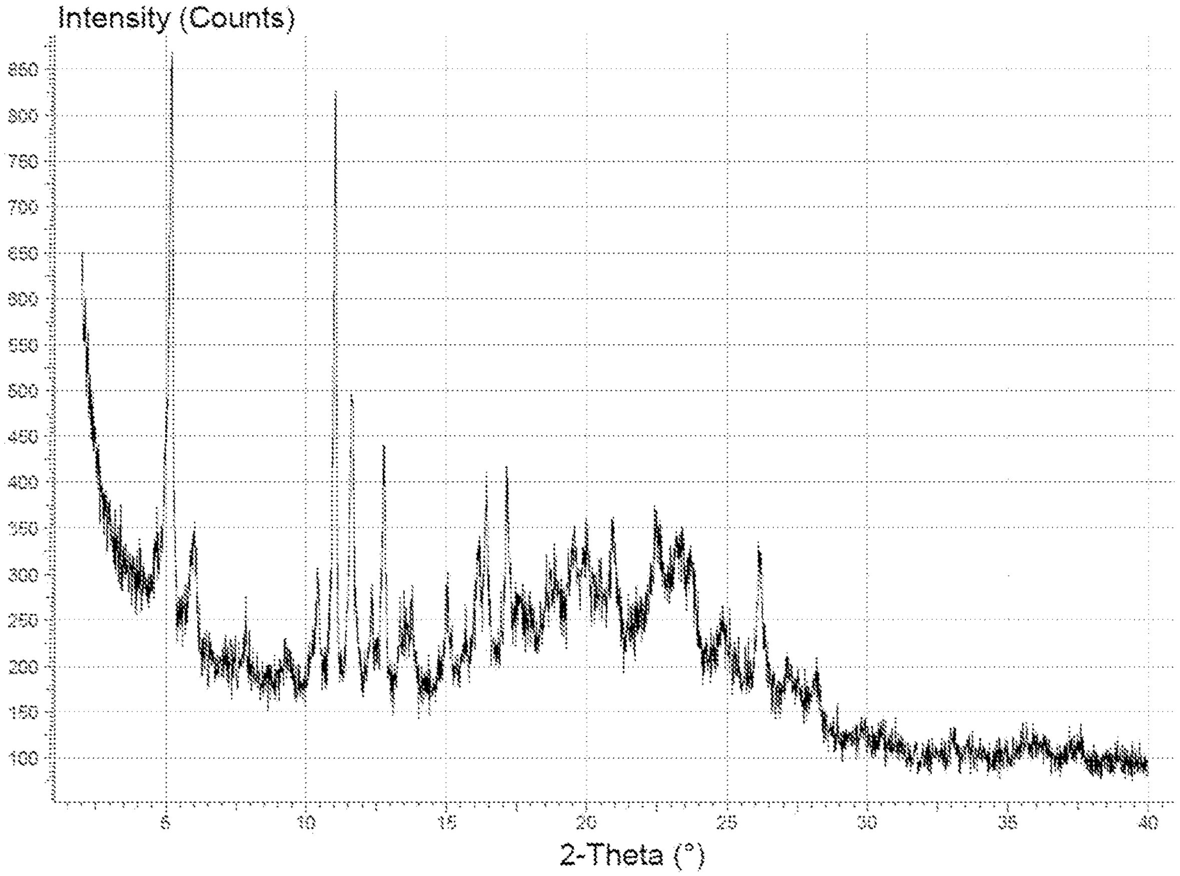

It was observed, as visualized in FIG. 4, that the exposure of the free acid in rat's plasma after administration of the free acid itself or the cholinate according to the invention to rats is similar at low doses up to 30 mg/kg. After administration of higher doses of the free acid, a much less than dose-proportional increase of exposure was observed. In contrast and surprisingly, after application of the cholinate salt, the plasma exposure of free acid as the active pharmaceutical ingredient showed a dose-proportional increase of exposure up to a dose of approximately 100 mg/kg. At higher doses (249 and 495 mg/kg, a less than dose-proportional increase of exposure was observed also after application of the cholinate. However, the exposure was still significantly higher compared to that after application of 100 mg/kg of the free acid in terms of absolute as well as dose normalized AUC (see Table 4 and FIGS. 9 and 10). Accordingly, with the cholinate salt it was surprisingly possible to achieve exposures in rats sufficiently high for toxicological studies while the application of the free acid reaches a plateau of plasma exposure at a level not suited for the toxicological studies.

Example 14: Solubility of Cholinate Vs Free Acid and Other Salts (in $Mg_{free\ acid}$/L)

Method

Investigation of the Solubility of the respective salts was proceeded as follows:

The solubility of the crystalline 2-(1-cyclobutyl-1H-pyrazol-4-yl)-5-[({1-[2-fluoro-4-(trifluoromethyl)phenyl] cyclopropyl} carbonyl)amino]benzoic acid (free acid) prepared as described in Example 3 of WO 2018/114786 A1, cholinate form A, prepared according to Example 1b herein, partially crystalline sodium salt, obtained as described in Example 6 herein, amorphous potassium salt, according to Example 8 herein and amorphous arginine salt, according to Example 9 herein, was determined according to the shake-flask method (according to Ph. Eur. at 1 mL scale, stirred overnight) at 25° C. unless mentioned differently.

Preparation of FaSSIF (Fasted State Simulated Intestinal Fluid) blank solution: 4.2 g NaOH, 44.7 g $NaH_2PO_4$*2 $H_2O$, and 61.86 g NaCl were dissolved in approximately 9.5 L demineralized water. Then, the pH of this solution was adjusted to 6.50+/−0.05 using HCl or NaOH, respectively. In the last step, the final volume was adjusted to 10.0 L by the addition of demineralized water.

Preparation of the final FaSSIF solution: 4.48 g SIF (Simulated Intestinal Fluids) powder (provider: biorelevant-.com, Product code: FFF01 (May 2022)) were dissolved in approximately 500 mL FaSSIF blank solution, then the final volume was adjusted to 2.0 L by the addition of FaSSIF blank solution. After 2 hours, the solution was considered to be ready to use and was used within 48 hours.

Preparation of FeSSIF (Fed State Simulated Intestinal Fluid) blank solution: 40.4 g NaOH, 118.74 g NaCl, and 82.4 mL glacial acetic acid were dissolved in approximately 9.5 L demineralized water. Then, the pH of this solution was adjusted to 5.00+/−0.05 using HCl or NaOH, respectively. In the last step, the final volume was adjusted to 10.0 L by the addition of demineralized water.

Preparation of the final FeSSIF solution: 22.4 g SIF powder (provider: biorelevant.com, Product code: FFF01 (May 2022)) were dissolved in approximately 500 mL FeSSIF blank solution, then the final volume was adjusted to 2.0 L by the addition of FeSSIF blank solution. The solution was considered to be ready to use immediately after manufacturing and was used within 48 hours.

Results

TABLE 5 solubility of the free acid, the cholinate, the sodium, potassium and arginin salt in $mg_{free\ acid}$/L.

| Solvent | Free acid | Cholinate Form A | Sodium salt | Potassium salt | Arginine Salt |
|---|---|---|---|---|---|
| Water | 8 | 10232 | 6176 | 6425 | 8172 |
| Buffer pH 8 | 968 | >10317 | 5075 | >11594 | >9209 |
| Buffer pH 7 | 146 | 917 | 421 | 684 | 794.9 |
| Buffer pH 4.5 | <1 | 7 | 3 | 5 | 7 |
| 0.1M HCL | n.d. | n.d. | n.d. | n.d. | n.d. |
| FeSSIF (37° C.) (Fed State Simulated Intestinal Fluid) | 10 | 21 | 14 | 24 | 26 |
| FaSSIF (37° C.) (Fasted State Simulated Intestinal Fluid) | 70 | 2053 | 426 | 781 | 1728 |

It was observed, that the aqueous solubility of the salts is significantly higher than the solubility of the free acid, including the measurements at pH 4.5 and above, as well as biorelevant media (FeSSIF and FaSSIF).

Surprisingly the cholinate, which was the only fully crystalline salt obtained, shows in most aqueous solvents tested a higher solubility than the amorphous or partially crystalline salts, in particular in FaSSIF.

It was unexpected that a salt in a crystalline form had a higher solubility than a salt in an amorphous form.

Example 15—Hygroscopy of Cholinate Vs. Free Acid and Other Salts

Method

Water sorption isotherms were determined using a DVS Resolution gravimetric sorption analyzer (London, UK), or a DVS Intrinsic instrument (Surface measurement Systems). The sample was dried for 1000 minutes at 0% relative humidity (R.H.). Afterwards the dry weight was recorded. The humidity was increased in steps of 10% to 90%, then increased to 95%, finally decreased again to 0% R.H. following the same steps. The equilibrium criterion for each relative humidity set point was 0.002% per minute relative mass change as a function of time. Dynamic vapour sorption isotherms are shown in FIG. 11*a* to 11*e*.

TABLE 6

Dynamic vapour sorption of cholinate vs. free acid and other salts - detailed measurement

| Change in mass [%] | Free acid | | Cholinate Form A | | Sodium Salt | | Potassium Salt | | Arginine Salt | |
|---|---|---|---|---|---|---|---|---|---|---|
| at | S | D | S | D | S | D | S | D | S | D |
| 0% Relative humidity | 0.06 | 0.65 | 0.00 | −0.14 | 0.00 | −3.95 | 1.84 | 67.05 | 0.00 | 31.74 |
| 10% Relative humidity | 0.08 | 0.52 | 0.36 | 2.50 | 0.85 | −0.87 | 3.33 | 36.40 | 1.39 | 20.17 |
| 20% Relative humidity | 0.10 | 0.42 | 0.56 | 3.59 | 1.36 | 0.84 | 4.12 | 21.86 | 2.13 | 12.15 |
| 30% Relative humidity | 0.12 | 0.35 | 0.75 | 5.08 | 1.92 | 1.91 | 5.53 | 15.18 | 2.98 | 10.78 |
| 40% Relative humidity | 0.14 | 0.29 | 0.95 | 6.98 | 2.95 | 3.33 | 8.59 | 11.85 | 4.25 | 10.09 |
| 50% Relative humidity | 0.17 | 0.16 | 1.21 | 9.30 | 7.77 | 5.07 | 11.39 | 9.24 | 5.72 | 9.59 |
| 60% Relative humidity | 0.20 | 0.09 | 1.61 | 12.14 | 11.23 | 7.95 | 14.10 | 6.66 | 7.20 | 9.10 |
| 70% Relative humidity | 0.23 | 0.05 | 2.11 | 16.02 | 15.05 | 11.79 | 17.79 | 4.31 | 9.40 | 6.12 |
| 80% Relative humidity | 0.29 | 0.03 | 3.05 | 21.87 | 20.22 | 16.87 | 24.21 | 2.92 | 13.25 | 4.54 |
| 90% Relative humidity | 0.44 | 0.01 | 18.30 | 33.33 | 30.67 | 26.84 | 37.54 | 1.40 | 20.10 | 2.87 |
| 95% Relative humidity | 0.65 | 0.00 | 46.21 | 46.21 | 42.62 | 42.62 | 67.05 | 0.00 | 31.74 | 1.60 |

(S = Sorption, D = Desorption)

TABLE 7

Dynamic vapour sorption of cholinate vs free acid and other salts-summarized results

| Exp. Condition | Free acid | Cholinate | Na Salt | K Salt | Arginin Salt |
|---|---|---|---|---|---|
| DVS Dm @ 30% R.H. (Sorption) | | 0.8% | 1.9% | 5.5% | |
| DVS Dm @ 50% R.H. (Sorption) | | 1.2% | 5.1% | 11.4% | |
| DVS Dm @ 80% R.H. (Sorption) | | 3.1% | 20.2% | 24.2% | |

Result

The isotherm plots of the DVS measurements are presented FIG. 11 *a-e*. Comparing the salts, the cholinate was less hygroscopic than the other salts, in particular in the normal range of atmospheric relative humidity (30-50%). The cholinate also exhibited a less pronounced increase at high relative humidities (>80%) than the other salts.

Example 16: Dissolution Profile of Cholinate Vs. Free Acid and Other Salts

Method

Prior to the measurements, the samples were micronized using a jet mill (MC DECJET 30) under nitrogen, with a pressure of 4.5 Bar for the injector and 4.0 Bar grinding pressure.

Dissolution rates of the drug substance were then determined using a flow through cell (FTC) from Sotax. All experiments were conducted in triplicates.

In the experiment, a cell was filled with an amount of solid that corresponds to 1 mg of the free acid (+/−2%, relating to the free acid). Then, the respective medium (FaSSIF or FeSSIF) was pumped through the cell with a pump rate of 2 mL/min for a total time of 14 minutes, resulting in a total volume of 28 mL. This volume was collected in time increments of 2 minutes, leading to 7 collected fractions with 4 mL each. The drug substance concentration of each fraction was determined by HPLC (external standard). The collected data resulted in the time-dependent concentration profiles which were used to compare the salts.

Result

The dissolution curves measured in FeSSIF and FaSSIF are presented FIG. 12*a-e*.

Figure 13A:
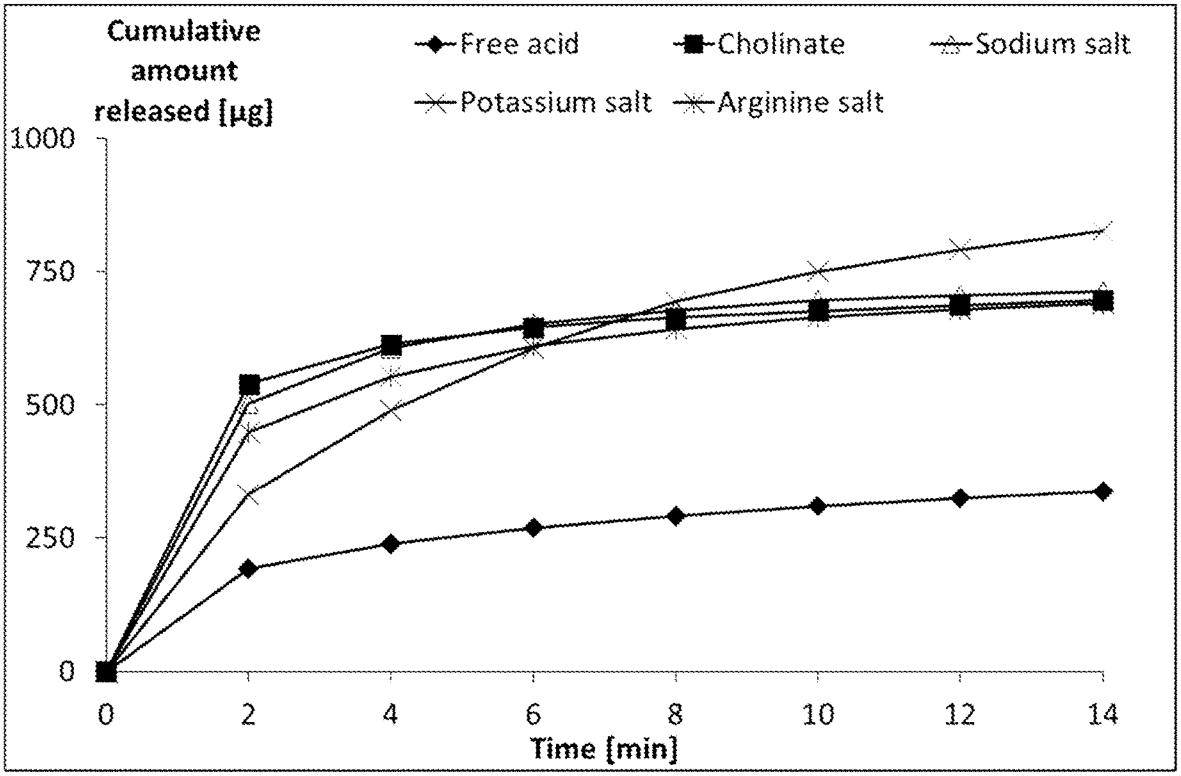

FIG. 13*a* is an overlay of the dissolution curves of the free acid and different salt forms in FeSSIF. The dissolution of the free acid was significantly slower as well as the cumulative amount dissolved after 14 minutes was lower compared to the salt forms. With the exception of the potassium salt, the salt forms showed similar dissolution profiles in FeSSIF.

Figure 13B:
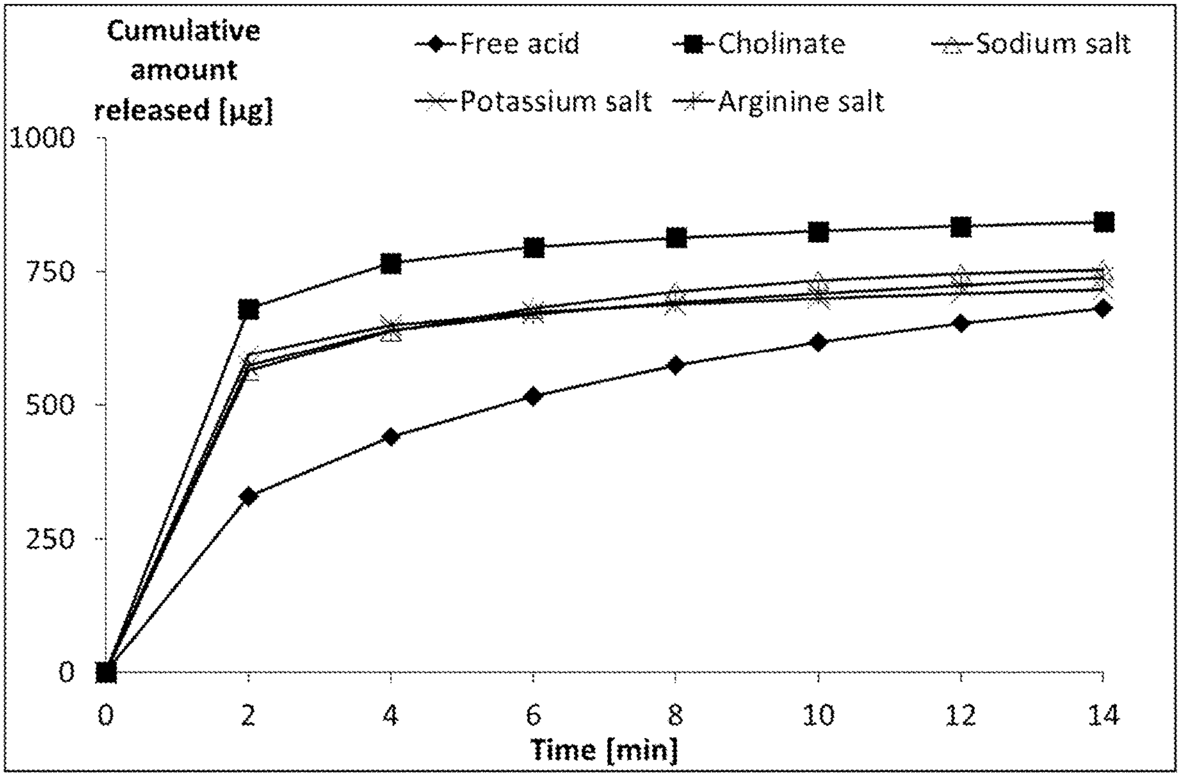

FIG. 13*b* is an overlay of the dissolutions curves of the free acid and the different salt forms in FaSSIF. Again the free acid dissolved slower and the cumulative amount dissolved after 14 minutes was lower compared to the other salts. Surprisingly, despite being crystalline, the cholinate showed a better dissolution profile than the other salts.

There were no differences between the dissolution profile of the sodium salt that is partially crystalline compared to the potassium and arginine salts that are amorphous.

Unexpectedly, the crystalline cholinate salt not only dissolved faster than the free acid but also than the other salts of the compound, which were only obtained in partially crystalline or amorphous form.

The invention claimed is:

1. A cholinate of 2-(1-cyclobutyl-1H-pyrazol-4-yl)-5-[({1-[2-fluoro-4 (trifluoromethyl)phenyl]-cyclopropyl}carbonyl)amino]benzoic acid.

2. The cholinate according to claim 1, wherein the cholinate is according to formula (II):

(II)

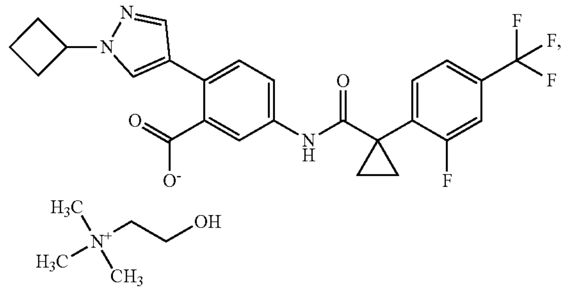

or a solvate, hydrate or tautomer thereof.

3. The cholinate according to claim 1, which is in crystalline form.

4. The crystalline cholinate according to claim 3, which is polymorphic form A.

5. The crystalline cholinate according to claim 3, characterized by the substantially same X-ray powder diffraction (XRPD) pattern as in FIG. 1.

6. The crystalline cholinate according to claim 3, characterized by a X-ray powder diffractogram measured at 25° C. and with Cu—K alpha 1 as radiation source displaying at least the following reflections, quoted as 2Θ value±0.2°: 12.99°, 20.42°, and 20.64°.

7. The crystalline cholinate according to claim 3, characterized by a X-ray powder diffractogram measured at 25° C. and with Cu—K alpha 1 as radiation source displaying at least the following reflections, quoted as 2Θ value±0.2°: 12.99°, 20.42°, 20.64°, 18.84°, and 22.32°.

8. The crystalline cholinate according to claim 3, characterized by a X-ray powder diffractogram measured at 25° C. and with Cu—K alpha 1 as radiation source displaying at least the following reflections, quoted as 2Θ value: 12.99°, 20.42°, 20.64°, 18.84°, 22.32°, 15.74°, and 20.75°.

9. The crystalline cholinate according to claim 3, characterized by the substantially the same IR pattern as in FIG. 2.

10. The crystalline cholinate according to claim 3, characterized by an IR pattern displaying at least the following bands, quoted as peak maxima in $cm^{-1}$: 1123, 1309, 1083.

11. The crystalline cholinate according to claim 3, characterized by an IR pattern displaying at least the following bands, quoted as peak maxima in $cm^{-1}$: 1123, 1309, 1083, 1324, and 808.

12. The crystalline cholinate according to claim 3, characterized by an IR pattern displaying at least the following bands, quoted as peak maxima in $cm^{-1}$: 1123, 1309, 1083, 1324, 808, 1091, and 874.

13. The crystalline cholinate according to claim 3, characterized by an IR pattern displaying at least the following bands, quoted as peak maxima in $cm^{-1}$: 1123, 1309, 1083, 1324, 808, 1091, 874, 1530, 954, and 835.

14. A method of preparing the cholinate according to claim 1, said method comprising the step of adding to a compound of formula (I):

(I)

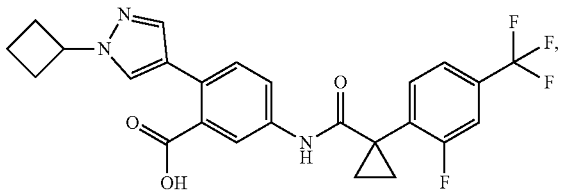

a compound of formula (III):

(III)

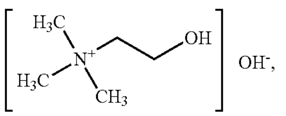

thereby forming said cholinate of formula (II):

(II)

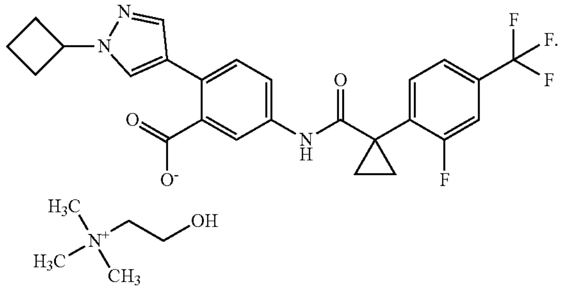

15. The method according to claim 14, wherein the method further comprises the steps of:

a) dissolving the cholinate of formula (II) in a solvent selected from the group consisting of acetonitrile, ethanol, methyl tert-butyl ether, ethyl acetate, heptane, toluene, tetrahydrofuran, butanol, acetone, water and mixtures thereof, to form a solution;

b) cooling the solution to precipitate the crystalline cholinate; and, c) filtering the resulting crystalline cholinate from the solution.

16. A pharmaceutical composition comprising a cholinate according to claim 1, and a pharmaceutically acceptable diluent or carrier.

17. A method of treating a disease selected from the group consisting of diabetic neuropathic pain, interstitial cystitis/bladder-pain-syndrome, endometriosis, and endometriosis-associated pain, comprising the step of administering the cholinate of claim 1 in a pharmaceutical dosage form to a patient in need thereof.

18. The method of claim 17, wherein said pharmaceutical dosage form comprises the cholinate and a pharmaceutically acceptable diluent or a carrier.

* * * * *